United States Patent
Trembly et al.

(10) Patent No.: US 10,485,481 B2
(45) Date of Patent: Nov. 26, 2019

(54) SYSTEMS AND METHODS FOR ENHANCING UPTAKE OF THERAPEUTIC AGENT FROM BLOODSTREAM INTO DISEASE SITE

(71) Applicant: THE TRUSTEES OF DARTMOUTH COLLEGE, Hanover, NH (US)

(72) Inventors: B. Stuart Trembly, Hanover, NH (US); Michael D. Nieskoski, Danvers, MA (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 100 days.

(21) Appl. No.: 15/559,901

(22) PCT Filed: Mar. 18, 2016

(86) PCT No.: PCT/US2016/023251
§ 371 (c)(1),
(2) Date: Sep. 20, 2017

(87) PCT Pub. No.: WO2016/154050
PCT Pub. Date: Sep. 29, 2016

(65) Prior Publication Data
US 2018/0070880 A1    Mar. 15, 2018

Related U.S. Application Data

(60) Provisional application No. 62/136,082, filed on Mar. 20, 2015.

(51) Int. Cl.
*A61M 37/00* (2006.01)
*A61M 1/00* (2006.01)
(Continued)

(52) U.S. Cl.
CPC .......... *A61B 5/6848* (2013.01); *A61B 5/0071* (2013.01); *A61B 5/036* (2013.01);
(Continued)

(58) Field of Classification Search
CPC ........ A61M 1/0088; A61M 2205/3306; A61M 5/142; A61B 5/036; A61B 5/026; A61B 5/0515; A61B 5/06; A61B 17/00022
See application file for complete search history.

(56) References Cited

U.S. PATENT DOCUMENTS 5,241,969 A    9/1993  Carson et al.
5,701,910 A   12/1997  Powles et al.
(Continued)

FOREIGN PATENT DOCUMENTS

WO    WO 1997/003715    2/1997

OTHER PUBLICATIONS

Stoherer, et al. "Onconic Pressure in Solid Tumors is Elevated", Aug. 1, 2000, Cancer Research 60, 4251-4255 (Year: 2000).*
(Continued)

*Primary Examiner* — Rebecca E Eisenberg
(74) *Attorney, Agent, or Firm* — Lathrop Gage LLP

(57) ABSTRACT

A method for enhancing uptake of a therapeutic agent from the bloodstream of a patient into a disease site of the patient includes applying negative pressure to the disease site to form a pressure differential favorable for transport of the therapeutic agent from the bloodstream into the disease site. A system for enhancing uptake of therapeutic agent from the bloodstream of a patient into a disease site of the patient includes (a) a partial enclosure with edge configured to interface with an exposed surface, of the patient and overlying the disease site, to seal the partial enclosure to the exposed surface, and (b) a pump for evacuating air from the partial enclosure to produce a partial vacuum in the partial
(Continued)

enclosure, to apply a negative pressure to the disease site so as to enhance uptake of the therapeutic agent into the disease site.

31 Claims, 11 Drawing Sheets

(51) Int. Cl.
*A61B 5/00* (2006.01)
*A61M 5/142* (2006.01)
*A61B 5/05* (2006.01)
*A61B 5/06* (2006.01)
*A61B 5/03* (2006.01)
*A61B 5/026* (2006.01)

(52) U.S. Cl.
CPC .............. *A61B 5/0515* (2013.01); *A61B 5/06* (2013.01); *A61M 1/0088* (2013.01); *A61M 5/142* (2013.01); *A61B 5/026* (2013.01); *A61M 2205/05* (2013.01); *A61M 2205/3306* (2013.01)

(56) References Cited

U.S. PATENT DOCUMENTS

| | | | |
|---|---|---|---|
| 5,722,985 A | 3/1998 | Pettus | |
| 5,888,530 A * | 3/1999 | Netti | A61M 5/14 424/423 |
| 6,254,614 B1 | 7/2001 | Jesseph | |
| 6,338,710 B1 | 1/2002 | Takahashi et al. | |
| 6,527,765 B2 | 3/2003 | Kelman et al. | |
| 7,470,240 B2 | 12/2008 | Schultheiss et al. | |
| 7,959,641 B2 | 6/2011 | Sorensen et al. | |
| 8,075,510 B2 | 12/2011 | Aklog et al. | |
| 8,109,956 B2 | 2/2012 | Shadeck | |
| 8,641,660 B2 | 2/2014 | Bonutti et al. | |
| 8,915,864 B2 * | 12/2014 | Quick | A61B 10/0275 600/566 |
| 8,915,894 B1 | 12/2014 | Lonky et al. | |
| 2003/0145849 A1 * | 8/2003 | Drinan | A61B 5/411 128/200.14 |
| 2005/0169969 A1 | 8/2005 | Li et al. | |
| 2006/0073101 A1 * | 4/2006 | Oldfield | A61K 49/0438 424/9.34 |
| 2008/0058630 A1 * | 3/2008 | Robertson | A61B 5/0031 600/368 |
| 2009/0234225 A1 * | 9/2009 | Martin | G01N 21/6428 600/431 |
| 2010/0266491 A1 * | 10/2010 | Farokhzad | A61K 9/5153 424/1.29 |
| 2011/0054365 A1 * | 3/2011 | Greener | A61M 1/0088 601/6 |

OTHER PUBLICATIONS

International Patent Application No. PCT/US2016/023251; International Search Report and Written Opinion dated Jul. 1, 2016; 18 pgs.
Wang et al. (2013), "Intra-Arterial Therapies for Metastatic Colorectal Cancer," Seminars in Interventional Radiology 2013, vol. 30, pp. 12-20.
Koyner et al. (2010), "Mechanical Ventilation and the Kidney," Blood Purification. 2010, vol. 29, pp. 52-68.
Stohrer et al. (2000), "Oncotic Pressure in Solid Tumors Is Elevated," Cancer Research 60, 4251-4255, Aug. 1, 2000.
DiResta et al (2000), "Artificial lymphatic system: A new approach to Reduce Interstitial Hypertension and Increase Blood Flow, pH and $pO_2$ in Solid Tumors," Annals of Biomedical Engineering, vol. 28, pp. 543-555.
DiResta et al. (2000), "Enhancing the Uptake of Chemotherapeutic Drugs into Tumors using an Artificial Lymphatic System," Annals of Biomedical Engineering, May 2000, vol. 28, Issue 5, pp. 556-564.
Brown et al. (2008), "Transdermal Drug Delivery Systems: Skin Perturbation Devices," Methods Mol Biol. 2008; 437:119-39.
Siegel et al. (2014), "Cancer Statistics, 2014," Ca—A Cancer Journal for Clinicians 64(1):9-29.
Netti et al. (1995), "Time-dependent behavior of interstitial fluid pressure in solid tumors: implications for drug delivery," Cancer Res. Nov. 15, 1995;55(22):5451-8.
Odland et al. (2005), "Use of tissue ultrafiltration for treatment of compartment syndrome—A pilot study using porcine hindlimbs," Journal of Orthopaedic Trauma 19:267-275.
Huynh et al. (2007), "Retro-convection enhanced delivery to increase blood to brain transfer of macromolecules," Brain Research 1128:181-190.
McKanna et al. (2016), "Clinician Panel Recommendations for Use of Negative Pressure Wound Therapy with Instillation," Ostomy Wound Management.
"Negative-pressure wound therapy," Wikipedia (2012), https://en.wikipedia.org/wiki/Negative-pressure_wound_therapy, Accessed Jun. 18, 2019.

* cited by examiner

SYSTEMS AND METHODS FOR ENHANCING UPTAKE OF THERAPEUTIC AGENT FROM BLOODSTREAM INTO DISEASE SITE

CROSS-REFERENCE TO RELATED APPLICATIONS

The present application is a 35 U.S.C. § 371 filing of International Application No. PCT/US2016/023251, filed Mar. 18, 2016, which claims the benefit of priority from U.S. Provisional Application Ser. No. 62/136,082 filed Mar. 20, 2015, which is incorporated herein by reference in its entirety.

BACKGROUND

According to a recent statistic, cancer is the cause of one in four deaths in the United States. The most prevalent cancer treatment methods are surgery, radiation, and chemotherapy. Additionally, the use of magnetic nanoparticle based hyperthermia treatment as a cancer treatment is increasing. In such hyperthermia treatment, magnetic nanoparticles are injected directly into the tumor at multiple different locations within the tumor to cover the full tumor volume. Subsequent heating of the nanoparticles by an external, alternating magnetic field can produce local temperatures sufficiently high to have therapeutic effect. Commonly, chemotherapy utilizes drugs infused into the patient's bloodstream. Frequently, two or more cancer treatment methods are used in combination.

Cancerous tumors are typically characterized by leaky vessels. As a consequence of the leaky vessels and impaired lymphatic drainage, as well as rapid growth, cancerous tumors are often associated with abnormally elevated tissue pressure. This elevated pressure impedes uptake, into the cancerous tumor, of therapeutic agents delivered via the bloodstream, thus reducing the efficacy of chemotherapy and magnetic nanoparticle based hyperthermia treatments. To compensate for this effect, a relatively large amount of therapeutic agent delivered must be administered to the patient, which may result in significant side effects. Alternatively, other treatment methods, such as surgery or radiation, must be employed.

SUMMARY

In an embodiment, a method for enhancing uptake of a therapeutic agent from the bloodstream of patient into a disease site of the patient includes applying negative pressure to the disease site to form pressure differential favorable for transport of the therapeutic agent from the bloodstream into the disease site.

In an embodiment, a system for enhancing uptake of a therapeutic agent from the bloodstream of patient into disease site of the patient includes a partial enclosure. The partial enclosure has an edge configured to interface with an exposed surface of the patient to seal the partial enclosure to the exposed surface, wherein the exposed surface overlies the disease site. The system further includes a pump for evacuating air from the partial enclosure to produce a partial vacuum in the partial enclosure, to apply a negative pressure to the disease site so as to enhance uptake of the therapeutic agent into the disease site.

DETAILED DESCRIPTION OF THE EMBODIMENTS

Figure 1:
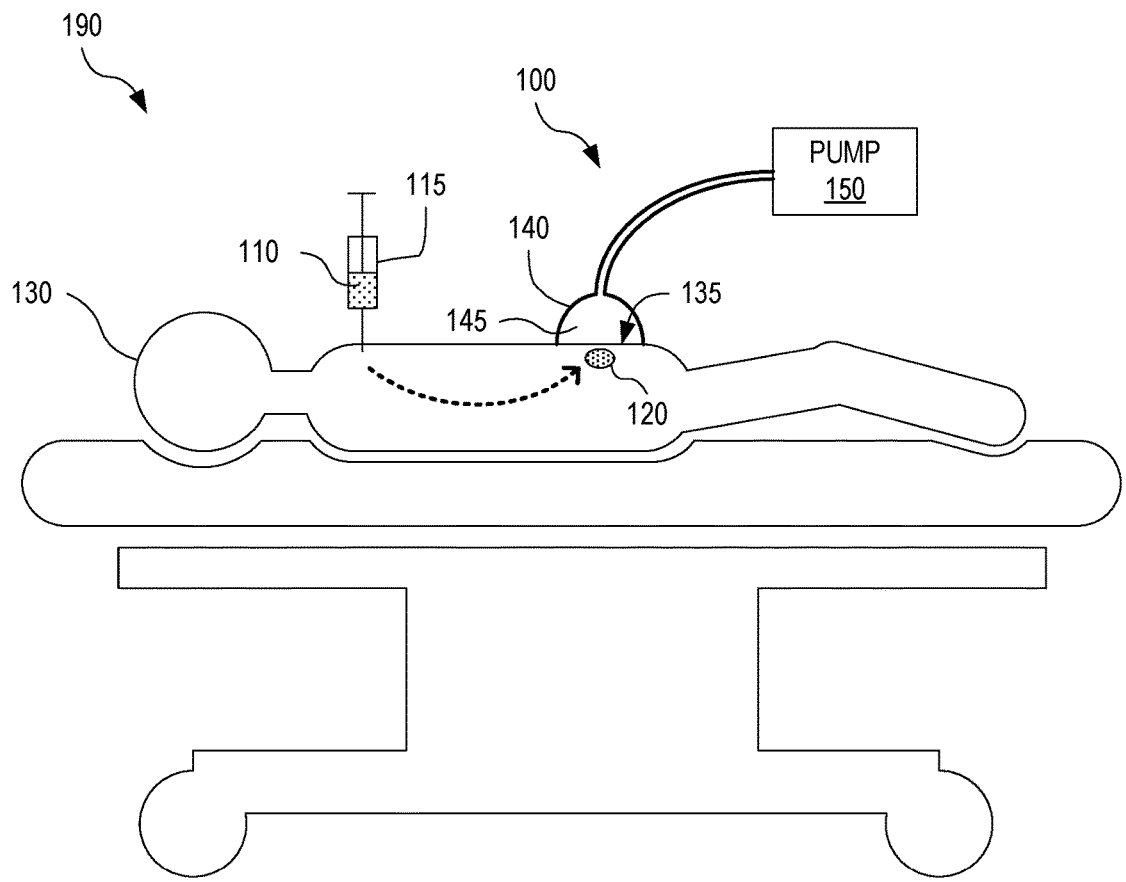
FIG. 1 illustrates a system for enhancing uptake of a therapeutic agent from the bloodstream into a disease site, according to an embodiment.

FIG. 1 illustrates one exemplary system 100 for enhancing uptake of a therapeutic agent from the bloodstream into a disease site. FIG. 1 shows system 100 in one exemplary use scenario 190, wherein system 100 enhances uptake of a therapeutic agent 110 from the bloodstream of a patient 130 into a disease site 120.

System 100 includes a partial enclosure 140 connected to a vacuum pump 150. Partial enclosure 140 is sealed to a surface 135 of patient 130 at disease site 120. Partial enclosure 140 includes one or more edges 142 configured to interface with surface 135 to form a seal. Vacuum pump 150 evacuates air from partial enclosure 140 to create a partial vacuum 145 within partial enclosure 140. Partial vacuum 145 acts upon surface 135 to apply a negative pressure in the tissue of patient 130 near surface 135. System 100 thus superimposes this negative pressure on the inherent tissue pressure to create a pressure differential between the bloodstream and the disease site more favorable for uptake of therapeutic agent 110 into disease site 120, as compared to the pressure differential associated with the inherent tissue pressure.

Herein, "pressure differential" refers to the pressure of a disease site measured relative to the pressure of the bloodstream near the disease site. A "pressure differential" may be positive, negative, or zero. Also herein, "inherent tissue pressure" refers to the pressure of the tissue in the absence of system 100, "negative pressure" refers to a pressure that is less than the atmospheric pressure, and "partial vacuum" refers to an environment having negative pressure. For example, a negative pressure (or a partial vacuum) may be −20 millimeters mercury (mmHg) gauge pressure. In this document, a pressure indicated in units of mmHg is a gauge pressure indicated relative to atmospheric pressure.

Disease site 120 may be (a) a cancerous tumor, (b) an infected area of patient 130 such as an area infected with *Staphylococcus aureus*, a toe infected with onychomycosis, (c) a disease site having elevated tissue pressure relative to atmospheric pressure, or (d) another type of disease site. Therapeutic agent 110 may be a chemotherapy drug, an agent for magnetic nanoparticle based hyperthermia treatment, an antifungal agent, an antibacterial agent, an antimicrobial agent, another therapeutic agent, or a combination thereof. In the case of hyperthermia treatment of a tumor, system 100 facilitates delivery of magnetic nanoparticles to the full tumor volume via a single injection into the bloodstream of patient 130, as opposed to the multiple injections into the tumor required conventionally.

Surface 135 is an exposed surface of patient 130, which may be an external surface of patient 130 (such as the skin of patient 130), an internal surface of patient 130 accessed through an orifice of patient 130, or a surgically accessed and/or surgically formed surface within patient 130.

In one embodiment, system 100 further includes a delivery device 115 for administering therapeutic agent 110 to the bloodstream of patient 130. Delivery device 115 includes, for example, a syringe and/or a catheter.

In one example of scenario 190, the inherent tissue pressure of disease site 120 is elevated relative to the surrounding inherent tissue pressure. Thus, in the absence of system 100, the inherent elevated pressure of disease site 120 creates a positive pressure differential between disease site 120 and the bloodstream. This positive pressure differential impedes transport of therapeutic agent 110 into disease site 120. However, system 100 applies a negative pressure to disease site 120, which reduces or eliminates the positive pressure differential to enhance uptake of therapeutic agent 110 into disease site 120, as compared to when the tissue pressure of disease site 120 is unaltered by system 100. With a certain strength of partial vacuum 145, system 100 may apply a negative pressure sufficient to form a negative pressure differential between disease site 120 and the bloodstream, to further enhance uptake of therapeutic agent 110 into disease site 120.

In another example of scenario 190, the inherent tissue pressure of disease site 120 is comparable to the surrounding inherent tissue pressure. In this case, system 100 applies a negative pressure to disease site 120 to form a negative pressure differential between disease site 120 and the bloodstream. This negative pressure differential leads to enhanced uptake of therapeutic agent 110 into disease site 120, as compared to when the tissue pressure of disease site 120 is unaltered by system 100.

Partial enclosure 140 is, in an embodiment, made of rubber, plastic, and/or one or more other materials suitable for sealing partial enclosure 140 onto surface 135. In certain embodiments, partial enclosure 140 includes biocompatible and/or latex-free materials. Partial enclosure 140 is sufficiently air tight that vacuum pump 150 is capable of producing and maintaining partial vacuum 145.

Figure 2:
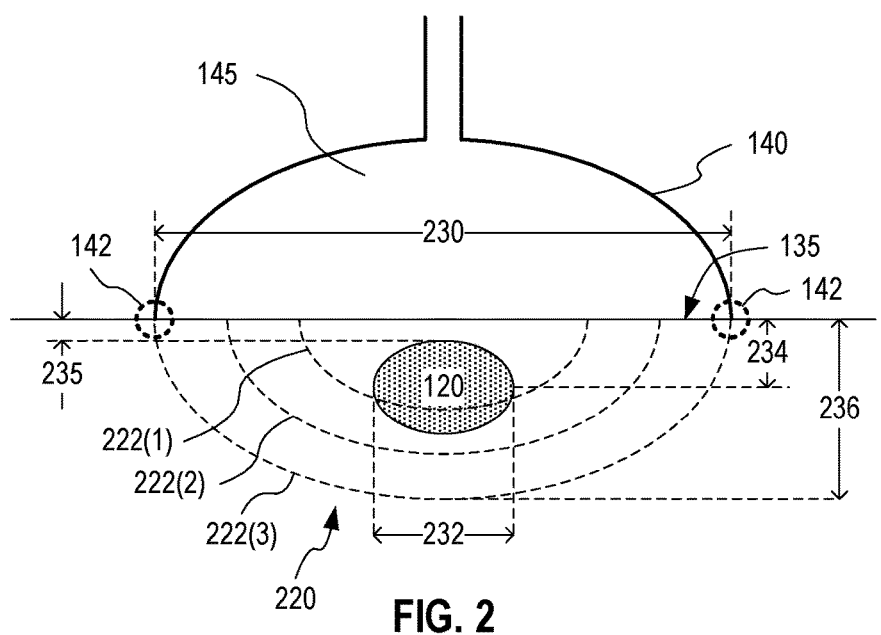
FIG. 2 illustrates the partial enclosure of the system of FIG. 1, and the effect of the system of FIG. 1 on the patient, in further detail, according to an embodiment.

FIG. 2 illustrates partial enclosure 140 (FIG. 1) and the effect of system 100 on patient 130 in further detail. Partial vacuum 145 superimposes a negative pressure 220 on the tissue below surface 135 and near partial enclosure 140. FIG. 2 depicts negative pressure 220 as equipressure contours 222(1), 222(2), and 222(3). Each equipressure contour 222 indicates a surface of spatially-constant negative pressure 220. Without departing from the scope hereof, equipressure contours 222 may have shape and extent different from those shown in FIG. 2.

Partial enclosure 140 is positioned on surface 135 overlying disease site 120. Although shown in FIG. 2 as being planar, surface 135 may be non-planar, without departing from the scope hereof. Partial enclosure 140 has a characteristic size 230 along surface 135. Characteristic size 230 may be on the order of millimeters or on the order of centimeters. Alternatively, characteristic size 230 and partial enclosure 140 may be configured to seal to a large portion of patient 130 such as a limb or the majority of patient 130. For example, edges 142 may form a seal that surrounds the nose and/or mouth of patient 130, with partial enclosure 140 applying partial vacuum 145 to all other portions of patient 130 than a region at the nose and/or mouth of patient 130. Disease site 120 has a characteristic size 232 along surface 135. One or both of characteristic sizes 230 and 232 are, for example, a diameter. Disease site 120 is located at a characteristic depth 234 relative to surface 135. Negative pressure 220 has a characteristic depth 236 into patient 130 away from surface 135. Characteristic depth 236 is, for example, the depth at which negative pressure 220 is 10% of its value at surface 135 or 1/e of its value at surface 135. Typically, characteristic depth 236 is a function of, at least, characteristic size 230 and the strength of partial vacuum 145. In the exemplary configuration shown in FIG. 2, characteristic depth 236 is greater than characteristic depth 234 and the projection (along direction perpendicular to surface 135) of disease site 120 onto surface 135 is within partial enclosure 140 such that system 100 exposes all of disease site 120 to negative pressure 220. Since negative pressure 220 penetrates into the tissue of patient 130, disease site 120 need not be in contact with surface 135. Disease site 120 may be spaced from surface 135 by a minimum distance 235. Minimum distance 235 is, for example, a fraction of a millimeter, on order millimeters, or on order centimeters. Alternatively, minimum distance is zero.

In one embodiment, partial enclosure 140 is rigid except for having flexible sealing edges 142. In this embodiment, the rigid portion of partial enclosure 140 may be composed, at least in part, of a polymer such as polyvinyl chloride (PVC), polyacrylate (Acrylic, PMMA), and/or polyetheretherketone (PEEK), while flexible sealing edges 142 may be composed, at least in part, of plasticized PVC and/or silicone.

Without departing from the scope hereof, partial enclosure 140 may be configured with characteristic size 230 and partial vacuum 145 sufficient only to expose a portion of disease site 120 to negative pressure 220. For example, characteristic size 230 may be smaller than characteristic size 232, the projection of disease site 120 onto surface 135 may fall at least in part outside partial enclosure 140, and/or characteristic depth 234 may be greater than characteristic depth 236. Generally, the greatest enhancement of uptake of therapeutic agent 110 into disease site 120 is achieved when characteristic depth 234 is small relative to characteristic depth 236.

Normal healthy tissue typically has a tissue pressure in the range from −7 to +8 mmHg. However, a cancerous tumor may have elevated tissue pressure in the range from +7 to +38 mmHg. The blood pressure varies with location in the body due to pressure loss in the vessels and the effects of gravity. Typically, the blood pressure at the heart averages approximately 100 mmHg but decreases to about 20 mmHg in the capillaries and zero mmHg in the small veins. Therefore, in a case where disease site 120 is a cancerous tumor, negative pressure 220 is preferably at least as negative as −38 mmHg at the location of the tumor. The strength of partial vacuum 145 required to produce negative pressure 220 in this range depends on the characteristic depth 234 of the tumor. In one example, system 100 may produce a partial vacuum 145 of around −100 mmHg to apply a negative pressure 220 sufficient to fully counteract the elevated pressure of a cancerous tumor. In another example, partial vacuum 145 is in the range from −10 to −150 mmHg.

Figure 3:
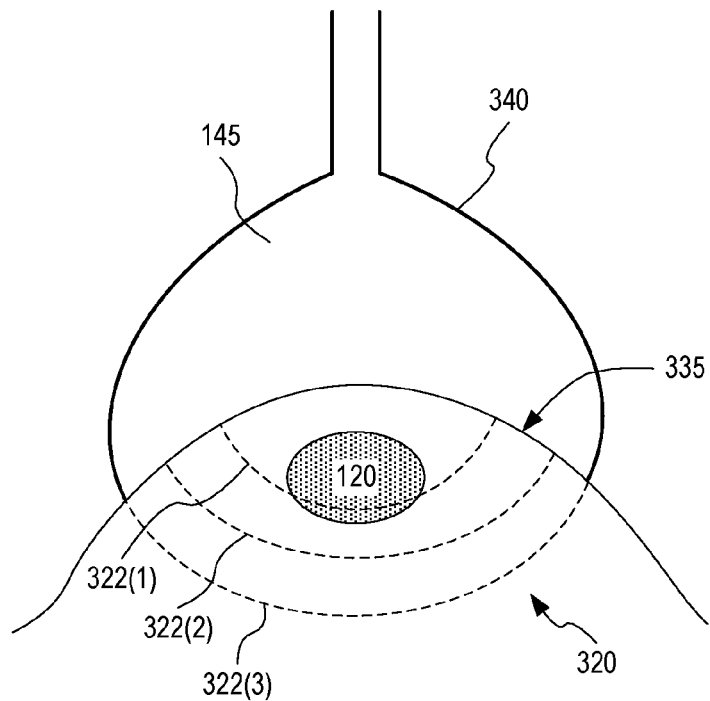
FIG. 3 illustrates a partial enclosure configured to interface with a generally convex surface overlying the disease site, according to an embodiment.

FIG. 3 illustrates a partial enclosure 340 configured to interface with a generally convex surface 335 overlying disease site 120. Partial enclosure 340 is an embodiment of partial enclosure 140 (FIG. 1), and surface 335 is an embodiment of surface 135. The configuration shown in FIG. 3 is an example of the configuration shown in FIG. 2, specifically tailored to cooperate with generally convex surface 335. Partial vacuum 145 forms a negative pressure 320 within patient 130 at the location of disease site 120. Negative pressure 320 is schematically indicated by equipressure contours 322 conceptually similar to equipressure contours 222.

Figure 4:
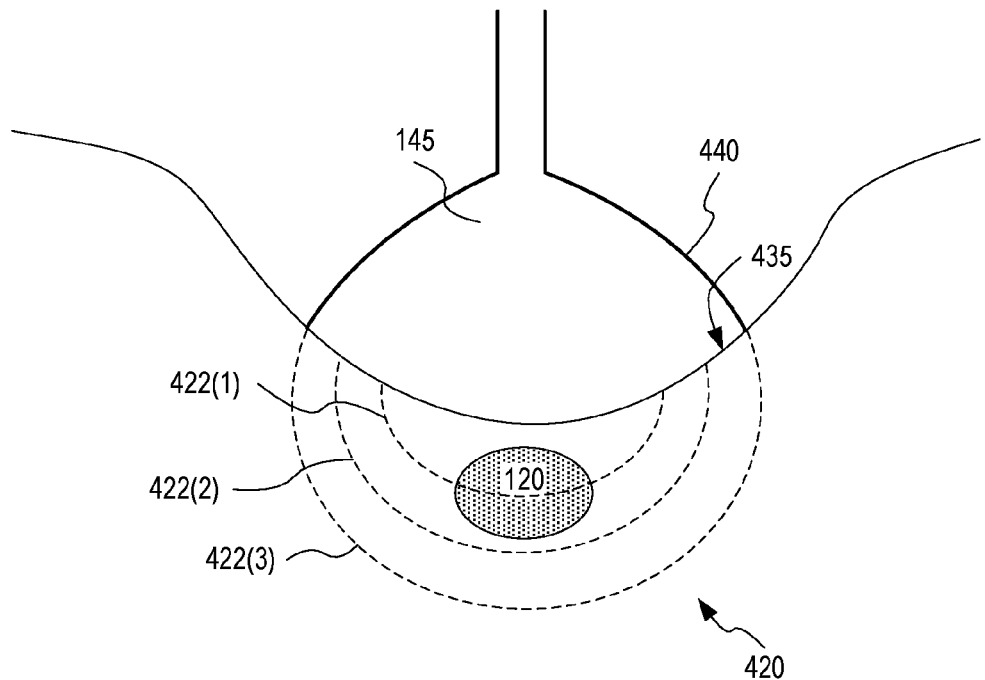
FIG. 4 illustrates a partial enclosure configured to interface with a generally concave surface overlying the disease site, according to an embodiment.

FIG. 4 illustrates a partial enclosure 440 configured to interface with a generally concave surface 435 overlying disease site 120. Partial enclosure 440 is an embodiment of partial enclosure 140 (FIG. 1), and surface 435 is an embodiment of surface 135. The configuration shown in FIG. 4 is an example of the configuration shown in FIG. 2, specifically tailored to cooperate with generally concave surface 435. Partial vacuum 145 forms a negative pressure 420 within patient 130 at the location of disease site 120. Negative pressure 420 is schematically indicated by equipressure contours 422 conceptually similar to equipressure contours 222.

Figure 5:
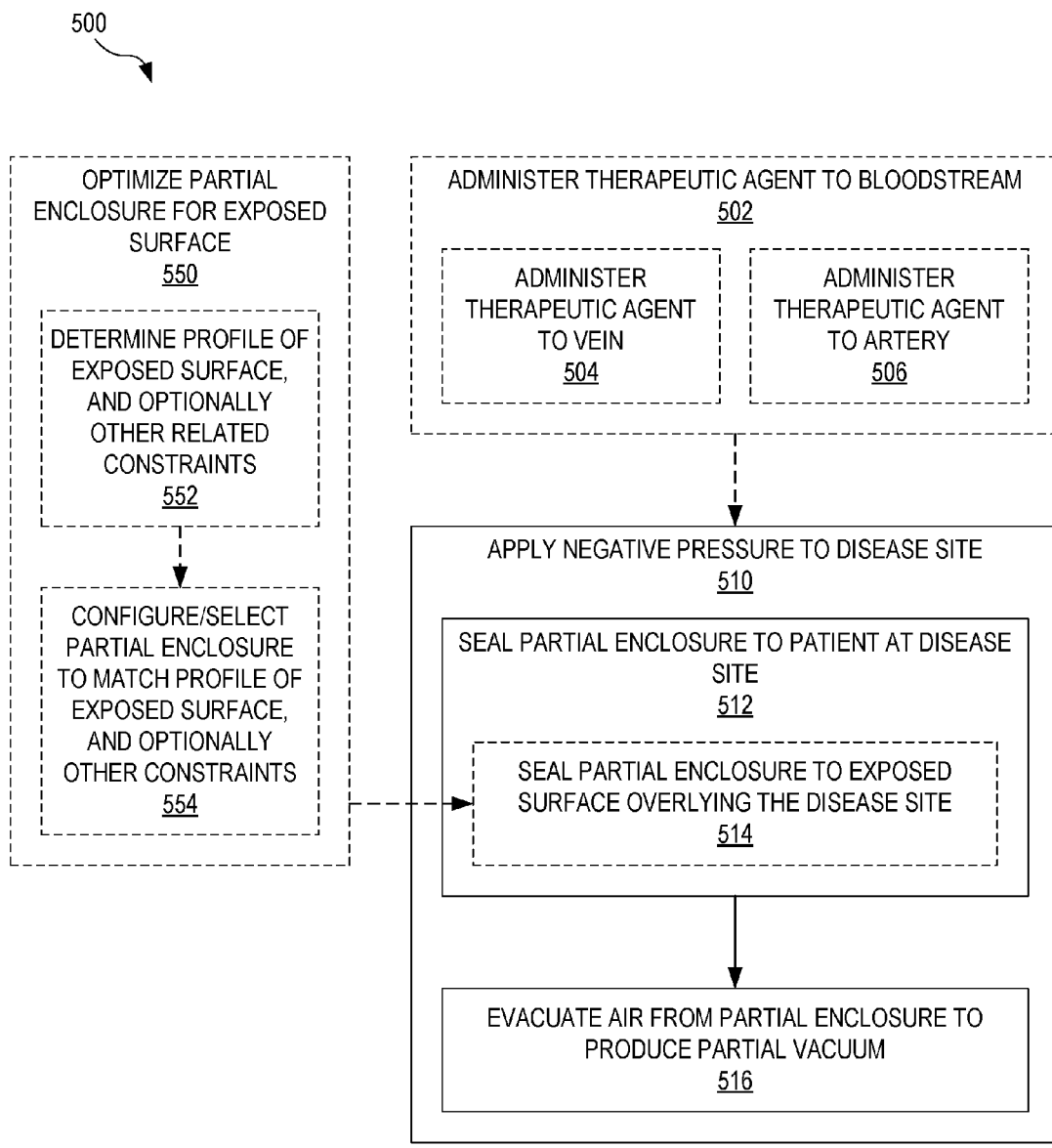
FIG. 5 illustrates a method for enhancing uptake of a therapeutic agent from the bloodstream into a disease site, according to an embodiment.

FIG. 5 illustrates one exemplary method 500 for enhancing uptake of a therapeutic agent from the bloodstream into a disease site. In one example, system 100 (FIG. 1) performs method 500 to enhance uptake of therapeutic agent 110 from the bloodstream of patient 130 into disease site 120.

In a step 510, method 500 applies a negative pressure to the disease site. In one example of step 510, system 100 applies negative pressure 220 (FIG. 2) to disease site 120. Step 510 includes steps 512 and 516.

In step 512, method 500 seals a partial enclosure to the patient at the disease site or near the disease site. Step 512 may include a step 514 of sealing the partial enclosure to an exposed surface overlying the disease site. In one example, of step 512, implemented with step 514, an operator or a robotic system seals partial enclosure 140 to surface 135, of patient 130, in a location overlying disease site 120, as shown in FIGS. 1 and 2.

In step 516, method 500 evacuates air from the partial enclosure to produce a partial vacuum within the partial enclosure. The partial vacuum results in the application of a negative pressure to at least a portion of the disease site. In one example of step 516, an operator or a control system activates vacuum pump 150 to produce partial vacuum 145, wherein partial vacuum 145 leads to the creation of negative pressure 220 at disease site 120.

Optionally, method 500 includes a step 502 of administering the therapeutic agent to the bloodstream of the patient. In one embodiment, step 502 includes a step 504 of administering the therapeutic agent to a vein of the patient. In one example of step 504, an operator or a robotic system uses delivery device 115 to inject therapeutic agent 110 into a vein of patient 130. In another embodiment, step 502 includes a step 506 of administering the therapeutic agent to an artery of the patient, wherein the artery is upstream (in terms of bloodflow) from the disease site. One example of step 506 utilizes a catheter, which is an embodiment of delivery device 115, to administer therapeutic agent 110 to an artery of patient 130, wherein the artery is upstream from disease site 120. In this example, an operator and/or a robotic system may insert and operate the catheter to access such an artery. For example, the operator and/or robotic system may, by utilizing techniques known in the art, insert the catheter into the femoral artery, the radial artery, or another large artery close to the surface of patient 130 and navigate the catheter to an artery upstream of disease site 120.

Typically, when administering the therapeutic agent into the vein of the patient, the therapeutic agent is transported to the heart of the patient and subsequently, through one or more arteries, to the disease site. Consequently, when performing step 504, the therapeutic agent is mixed with the blood carried to the heart by all veins such that, upon reaching the heart, the therapeutic agent is diluted into the entire blood volume of the patient. By contrast, when performing step 506 to administering agents through an artery, the therapeutic agent is delivered to the area of the disease site at substantially higher concentration.

In one example of method 500, the disease site is a tumor and the therapeutic agent is an enzyme intended to degrade the extra-cellular matrix of the tumor, such as hyaluronidase or collagenase. Generally, when such agents are taken up into a tumor from the vasculature, they may degrade the extra-cellular matrix of the tumor, which in turn may reduce the pressure within the tumor. This is a desirable effect that may enhance uptake of a therapeutic agent into the tumor. However, when the intra-tumoral pressure is reduced by application of negative pressure in step 510, fewer blood vessels within the tumor will collapse, and consequently greater amounts of a therapeutic agent injected at a later time may reach the tumor. In a related embodiment of method 500, step 502 is replaced by a step of injecting the enzyme directly into the tumor.

Without departing from the scope hereof, step 502 may be replaced by a step of administering the therapeutic agent directly to the disease site. For example, magnetic nanoparticles may be injected into one or more locations within the disease site, and application of negative pressure in step 510 may help disperse the magnetic particles within the disease site.

Although shown in method 500 as preceding application of negative pressure (step 510), administration of the therapeutic agent to the bloodstream (step 502) may take place before and/or during application of the negative pressure (step 510), without departing from the scope hereof. In certain embodiments, administration of the therapeutic agent to the bloodstream (step 502) is performed after sealing the partial enclosure to the patient at the disease site (step 512)

and before evacuating air from the partial enclosure to produce the partial vacuum (step 516). In such embodiments, the time of initiating step 516 may advantageously be such that production of partial vacuum 145, and thus application of negative pressure 220, coincides with arrival of the therapeutic agent to the area of the disease site. This particular timing may serve to at least partly overcome effects associated with self-limiting tissue pressure: With time, tissue tends to respond to an externally applied negative pressure (such as negative pressure 220) by counteracting the externally applied negative pressure to once again raise the tissue pressure. By delaying the performance of step 516 until the therapeutic agent arrives to the area of the disease site, optimal tissue pressure is achieved at the same time as optimal concentration of the therapeutic agent, such that uptake of the therapeutic agent into the disease site is optimally enhanced. These embodiments of method 500 may initiate step 516 a short period of time before arrival of the therapeutic agent to the disease site, to account for a delay between activation of the vacuum pump and actually achieving a partial vacuum of sufficient strength.

In an embodiment, method 500 includes a step 550 of optimizing the partial enclosure for the exposed surface utilized in step 514. Step 550 includes a step 552 of determining the profile of the exposed surface. In one example, step 552 determines whether the exposed surface is mostly planar, convex, concave, or a combination thereof. Step 552 may also include determining other constraints that influence the optimal shape or size of the partial enclosure. For example, a smaller partial enclosure may be required for accessing internal surfaces such as near the cervix, while a larger partial enclosure may be acceptable and/or preferable for sealing to a female breast. Step 550 further includes a step 554 of configuring or selecting the partial enclosure in accordance with the determination(s) made in step 552.

Figure 6:
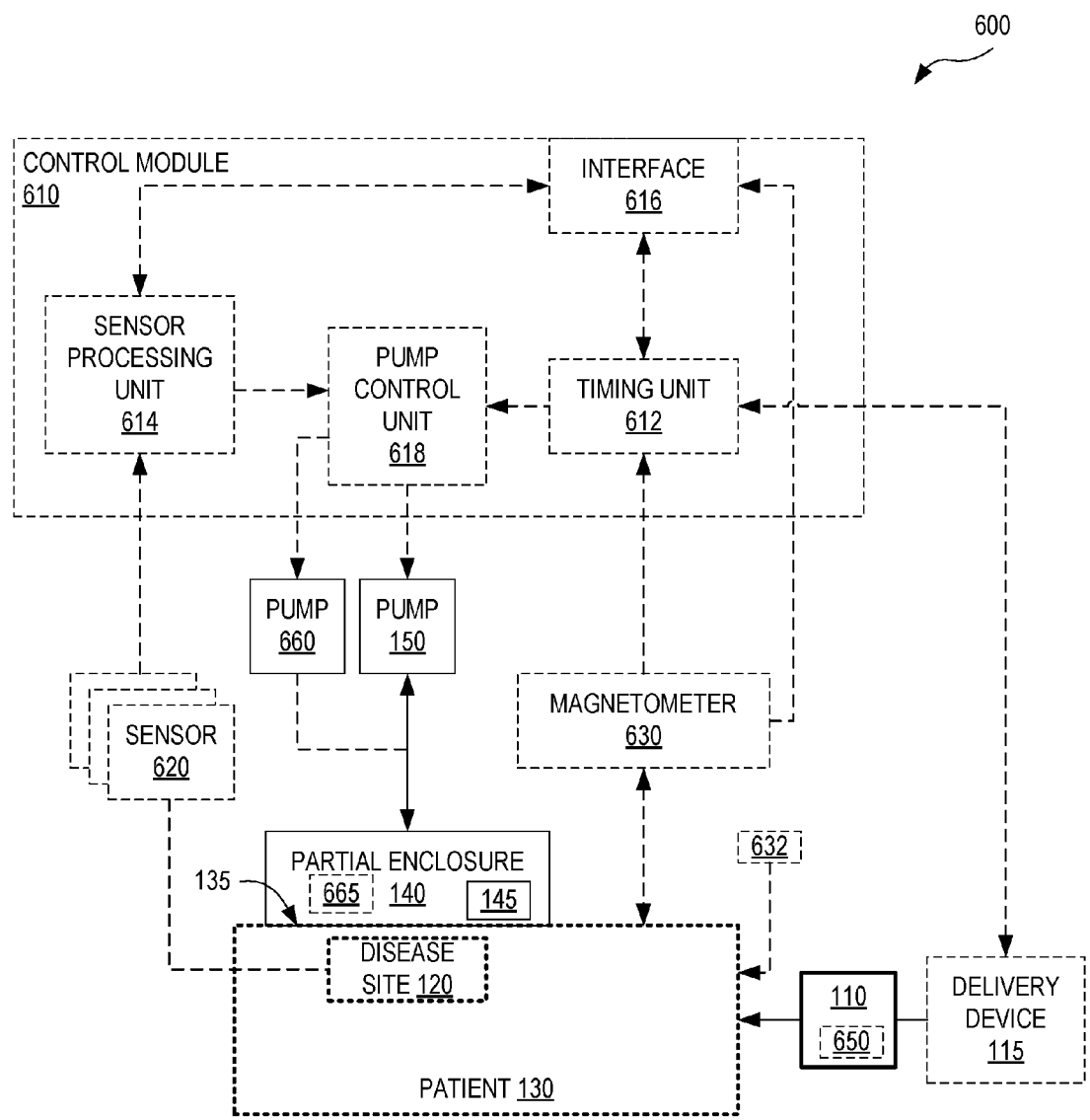
FIG. 6 illustrates another system for enhancing uptake of a therapeutic agent from the bloodstream into a disease site, according to an embodiment.

FIG. 6 illustrates one exemplary system 600 for enhancing uptake of a therapeutic agent from the bloodstream into a disease site such as disease site 120. System 600 is an embodiment of system 100 (FIG. 1) and may perform method 500 (FIG. 5).

System 600 includes partial enclosure 140 coupled with vacuum pump 150. As discussed in reference to FIGS. 1, 2, 3, and 4, partial enclosure 140 seals to surface 135 of patient 130 at or near disease site 120. System 600 may include delivery device 115, as discussed in reference to FIG. 1.

Optionally, system 600 includes one or more of a control module 610, a timing unit 612 implemented in control module 610, a pump control unit 618 implemented in control module 610, a magnetometer 630, one or more sensors 620, a sensor processing unit 614 that processes outputs from sensor(s) 620 and is implemented in control module 610, and an interface 616 implemented in control module 610.

In one embodiment, system 600 includes control module 610 with pump control unit 618 and timing unit 612. Timing unit 612 is communicatively coupled with pump control unit 618, and pump control unit 618 is communicatively coupled with vacuum pump 150. Optionally, timing unit 612 is also communicatively coupled with delivery device 115. Pump control unit 618 controls operation of vacuum pump 150 to produce partial vacuum 145. Pump control unit 618 may control the on/off-state of vacuum pump 150 as well as the pumping rate of vacuum pump 150. Via pump control unit 618, timing unit 612 controls the timing of pumping by vacuum pump 150. In one implementation, delivery device 115 is coupled with timing unit 612, and timing unit 612 activates vacuum pump 150 for a pre-specified duration after the time when delivery device 115 starts administering therapeutic agent 110 to the bloodstream of patient 130. This implementation may serve to avoid or reduce adverse impact from the self-limiting tissue pressure effect discussed in reference to FIG. 5. Optionally, timing unit 612 controls timing of operation of both vacuum pump 150 and delivery device 115. In one implementation, control module 610 includes interface 616, and interface 616 communicates timing information to an operator, or an external system, and/or receives timing information from an operator or an external system. In one such implementation, an operator or external system may communicate, via interface 616 to timing unit 612, a set delay between activation of delivery device 115 and activation of vacuum pump 150.

In another embodiment, system 600 includes magnetometer 630 communicatively coupled with the bloodstream of patient 130. Magnetometer 630 measures the magnetic field at the location of magnetometer 630 and is used in conjunction with a therapeutic agent 110 that includes a magnetic substance 650. Magnetometer 630 may include a magnetic field generator 632. In one example, magnetic field generator 632 generates a magnetic field and magnetometer 630 senses a change in response to this applied magnetic field, wherein the change is caused by the presence of magnetic substance 650. In one example, therapeutic agent 110 is a magnetic nanoparticle based hyperthermia treatment agent and includes magnetic nanoparticles, an example of magnetic substance 650, for magnetically induced heating of disease site 120. In another example, therapeutic agent 110 does not rely on magnetic substance 650 for therapeutic effect; rather, magnetic substance 650 is added to therapeutic agent 110 as a reporting agent detectable by magnetometer 630. Optionally, magnetometer 630 is communicatively coupled with timing unit 612, such that timing unit 612 may control operation of vacuum pump 150 based upon detection of magnetic substance 650 by magnetometer 630. In embodiments of system 600 that include magnetometer 630 and control module 610 with timing unit 612, control module 610 may further include interface 616. Interface 616 may (a) output one or both of magnetic field measurements by magnetometer 630 and related timing data to an operator or an external system, and/or (b) communicate to timing unit 612 a set delay between detection of magnetic substance 650 by magnetometer 630 and activation of vacuum pump 150.

Without departing from the scope hereof, magnetometer 630 may be replaced by a susceptometer, a magnetic imaging system, a magnetic particle imaging system, or other device capable of detecting a magnetic property change. Additionally, magnetic substance 630 and magnetometer 630 may be replaced by, or work in conjunction with, a fluorescent substance and an fluorescence detection device, respectively, wherein the fluorescence detection device is placed externally to patient 130 and optically detects the fluorescent substance, without departing from the scope hereof.

In yet another embodiment, system 600 includes one or more sensors 620 that are inserted into disease site 120 to measure one or more properties of disease site 120. Although FIG. 6 shows up to three sensors 620, system 600 may include any number of sensors 620. In one example, sensor(s) 620 include a pressure sensor that measures the tissue pressure at a location within disease site 120. System 600, or an operator, may utilize measurements made by such a pressure sensor to evaluate if partial vacuum 145 is of a suitable strength and, optionally, adjust operation of vacuum pump 150 to adjust the strength of partial vacuum 145. In another example, sensor(s) 620 include a blood perfusion sensor that measures blood perfusion at a location within disease site 120. System 600, or an operator, may utilize measurements made by such a blood perfusion sensor to evaluate if blood flow into disease site 120 is sufficient to achieve a certain degree of enhancement of uptake of therapeutic agent 110 into disease site 120. In one implementation, sensor(s) 620 is communicatively coupled with control module 610, and control module 610 includes a sensor processing unit 614 and interface 616. Sensor processing unit 614 processes output from sensor(s) 620 and communicates results to an operator or an external system via interface 616. Optionally, sensor processing unit 614 is communicatively coupled with pump control unit 618 such that system 600 may adjust operation of vacuum pump 150 based upon feedback from sensor(s) 620.

In one implementation, control module 610 is implemented with a processor and machine-readable instructions encoded in non-transitory memory. In this implementation, the machine-readable instructions, upon execution by the processor, perform at least a portion of the function of control module 610. In one example, the machine-readable instructions, upon execution by the processor, perform the function of timing unit 612. In another example, the machine-readable instructions, upon execution by the processor, perform at least a portion of the function of sensor processing unit 614.

In certain embodiments, system 600 further includes a pump 660 configured to generate a positive pressure 665 within partial enclosure 140. Positive pressure 665 acts upon surface 135 to apply a positive pressure in the tissue of patient 130 near surface 135. Herein, "positive pressure" refers to a pressure that is greater than the atmospheric pressure. A positive pressure applied to the tissue of patient 130, at or near disease site 120, may induce collapse of capillaries within disease site 120 to reduce blood flow away from disease site 120 and thereby reduce the flow of therapeutic agent away from disease site 120. Pump 618 may be controlled by pump control unit 618, for example according to information received from timing unit 612 and/or sensor processing unit 614. Without departing from the scope hereof, pumps 150 and 660 may be implemented as a single pump capable of generating both a positive and a negative pressure within partial enclosure 140. When utilizing partial enclosure 140 to apply a positive pressure, partial enclosure may be held onto patient 130 using, for example, a strap or a mount that affixes partial enclosure 140 to a table/chair on which patient 130 is located.

Without departing from the scope hereof, one, several, or all of timing unit 612, sensor processing unit 614, pump control unit 618, and interface 616 may be omitted from system 600 and replaced by a human operator.

Figure 7:
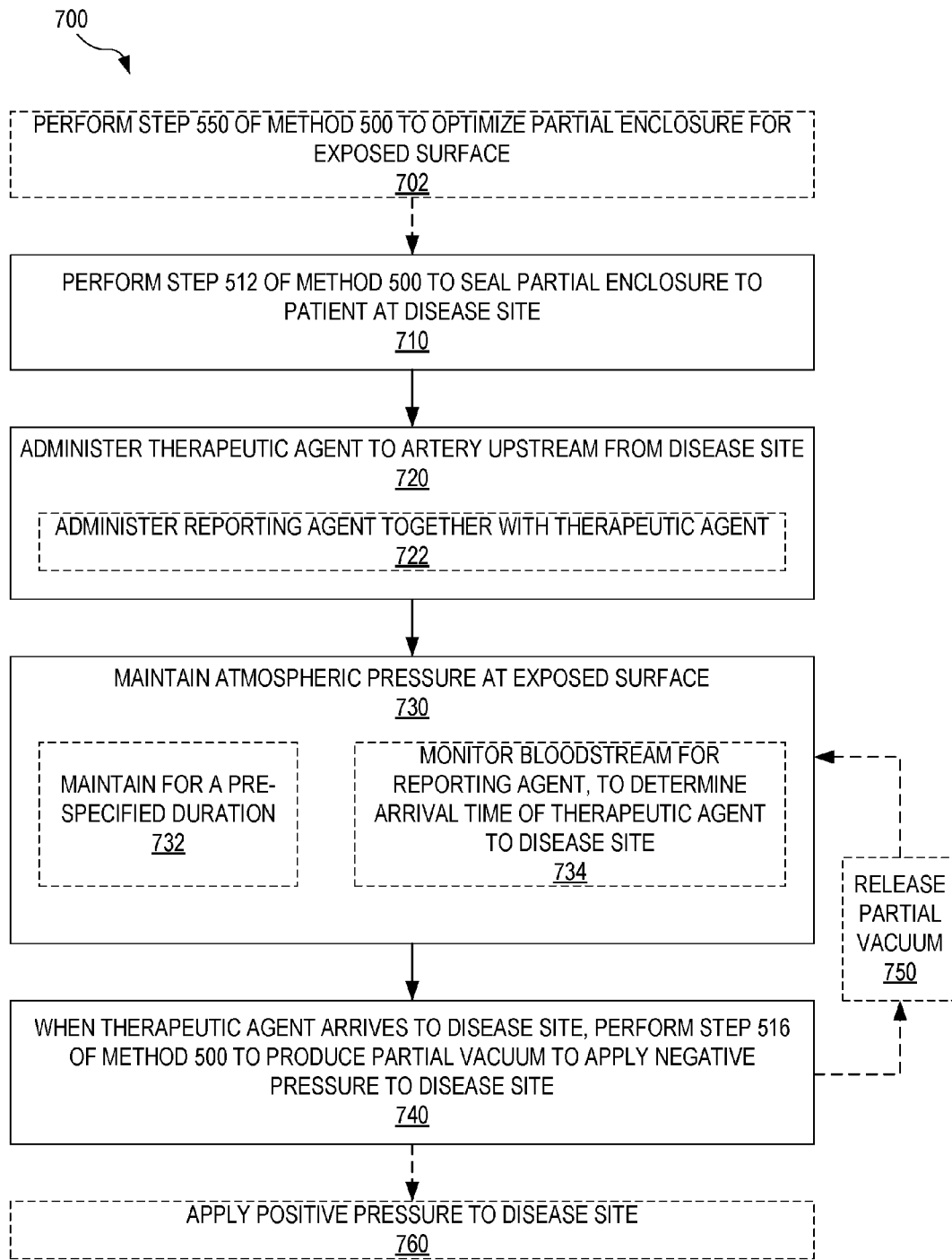
FIG. 7 illustrates a method for enhancing uptake of a therapeutic agent from the bloodstream into a disease site, wherein the therapeutic agent is administered to an artery that is upstream from the disease site, according to an embodiment.

FIG. 7 illustrates one exemplary method 700 for enhancing uptake of a therapeutic agent from the bloodstream into a disease site, wherein the therapeutic agent is administered to an artery that is upstream from the disease site. Benefits of administering the therapeutic agent to an artery upstream from the disease site are discussed in reference to FIG. 5. Method 700 is an embodiment of method 500 (FIG. 5) and is, for example, performed by system 600 (FIG. 6).

In a step 710, method 700 performs step 512 of method 500 to seal a partial enclosure to an exposed surface at or near the disease site, as discussed in reference to FIG. 5.

In a step 720, the therapeutic agent is administered to an artery that is upstream from the disease site, as discussed in reference to step 506 of method 500. Step 720 is an embodiment of step 502 implemented with step 506.

In a step 730, method 700 maintains substantially atmospheric pressure at the exposed surface used to seal the partial enclosure. In one example of step 730, pump control unit 618 maintains vacuum pump 150 in its off-state during step 730. Without departing from the scope hereof, the pressure within the partial enclosure may be less than atmospheric pressure during step 730, as long as this pressure is insufficient to induce the self-limiting tissue pressure effect discussed in reference to FIG. 5.

In a step 740, method 700 performs step 516 of method 500 to produce a partial vacuum in the partial enclosure, thus applying a negative pressure to the disease site, as discussed in reference to FIG. 5. Step 740 is an embodiment of step 516 of method 500. In one example of step 740, pump control unit 618 turns on vacuum pump 150. By performing step 730 prior to step 740, the self-limiting tissue pressure effect is at least minimized and possibly avoided. As a result, optimal tissue pressure at the disease site is achieved at the same time as optimal concentration of the therapeutic agent at the disease site. Without departing from the scope hereof, method 700 may initiate pumping on the partial enclosure in step 740 shortly before the therapeutic agent arrives to the disease site, in order to account for any delay between start of pumping and actually achieving the partial vacuum.

Without departing from the scope hereof, step 710 may be performed at any time before step 740, for example during step 730.

In one embodiment, step 730 includes a step 732 of maintaining the atmospheric pressure (or reduced pressure insufficient to induce the self-limiting tissue pressure effect) for a pre-specified duration. The pre-specified duration is, for example, a pre-calculated propagation time from (a) the location where the therapeutic agent is administered to (b) the location of the disease site.

In another embodiment, step 720 includes a step 722 and step 730 includes a step 734. In step 722, a reporting agent is administered together with the therapeutic agent. In one example of step 722, delivery device 115 administers magnetic substance 650 together with therapeutic agent 110. In step 734, the bloodstream is monitored for the arrival of the reporting agent to a certain location. In one implementation, the monitored location is at the disease site. In an example of this implementation, magnetometer 630 is positioned at disease site 120, and timing unit 612 prompts pump control unit 618 to activate vacuum pump 150 to perform step 740 upon detection of magnetic substance 650 at disease site 120. In a similar implementation, the monitored location is slightly upstream of the disease site. In an example of this implementation, magnetometer 630 is positioned slightly upstream of disease site 120, and timing unit 612 prompts pump control unit 618 to activate vacuum pump 150 to achieve a pre-specified partial vacuum 145 upon arrival of magnetic substance 650 at disease site 120. In another implementation, the monitored location is away and upstream from the disease site. In an example of this implementation, magnetometer 630 is positioned away and upstream from disease site 120. After detection of magnetic substance 650 by magnetometer 630, timing unit 612 introduces a pre-specified delay before prompting pump control unit 618 to activate vacuum pump 150, such that partial enclosure 140 achieves a pre-specified partial vacuum 145 upon arrival of magnetic substance 650 at disease site 120. The pre-specified delay introduced by timing unit 612 is set to substantially match the propagation time therapeutic agent 110 to disease site 120 from the bloodstream location monitored by magnetometer 630.

In certain embodiments, method 700 further includes a step 750 of releasing the partial vacuum from the partial enclosure before returning to step 730 and, subsequently, to step 740. These embodiments of method 700 are tailored to enhance uptake of remaining, recirculated therapeutic agent into the disease site. After the first pass to the area of the disease site associated with the first iteration of step 740, a portion of the therapeutic agent may be carried by veins to the heart, and recirculated to the area of the disease site. At this second pass and any subsequent passes, the recirculated therapeutic agent is diluted into the entire blood volume of the patient, and recirculated by one or more arteries to the area of the disease site. Although the first pass delivers the therapeutic agent to the area of the disease site at much higher concentration than the concentrations achievable with recirculated therapeutic agent, additional passes with diluted therapeutic agent may still have therapeutic effect on the disease site. To enhance uptake of recirculated therapeutic agent at the second pass, step 750 releases the partial vacuum after the first iteration of step 740 to avoid or reduce the self-limiting tissue pressure effect. Next, method 700 performs step 730, as discussed for the first pass, before performing a second iteration of step 740 coinciding with the second pass of the therapeutic agent to the area of the disease site. Method 700 may perform iterations of steps 750, 730, and 740 to enhance uptake of recirculated therapeutic agent to the disease site for two or more passes after the first pass.

Optionally, a step 702 precedes step 710. In step 702, method 700 performs step 550 of method 500 to optimize the partial enclosure for the exposed surface to which the partial enclosure is sealed.

In an embodiment, method 700 further includes a step 760 of applying a positive pressure to the disease site. This positive pressure may induce collapse of capillaries within the disease site to reduce blood flow away from the disease site, so as to improve the retention, within the disease site, of therapeutic agent taken up by the disease site in preceding step 740. Step 760 may hereby improve the efficacy of the therapeutic agent on the disease site. In one example of step 760, pump control unit 618 turns on pump 660 to generate positive pressure 665 within partial enclosure 140. Pump control unit 618 may perform this operation according to signals received from timing unit 612. In one such scenario, timing unit 612 introduces a pre-specified delay between step 740 and step 760. In another scenario, timing unit 612 performs step 760 immediately after completion of step 740 such that there is essentially no delay between (a) disease site 120 experiencing a negative pressure to enhance the uptake of therapeutic agent 110 and (b) disease site 120 experiencing a positive pressure to improve the retention of therapeutic agent 110 within disease site 120.

Figure 8:
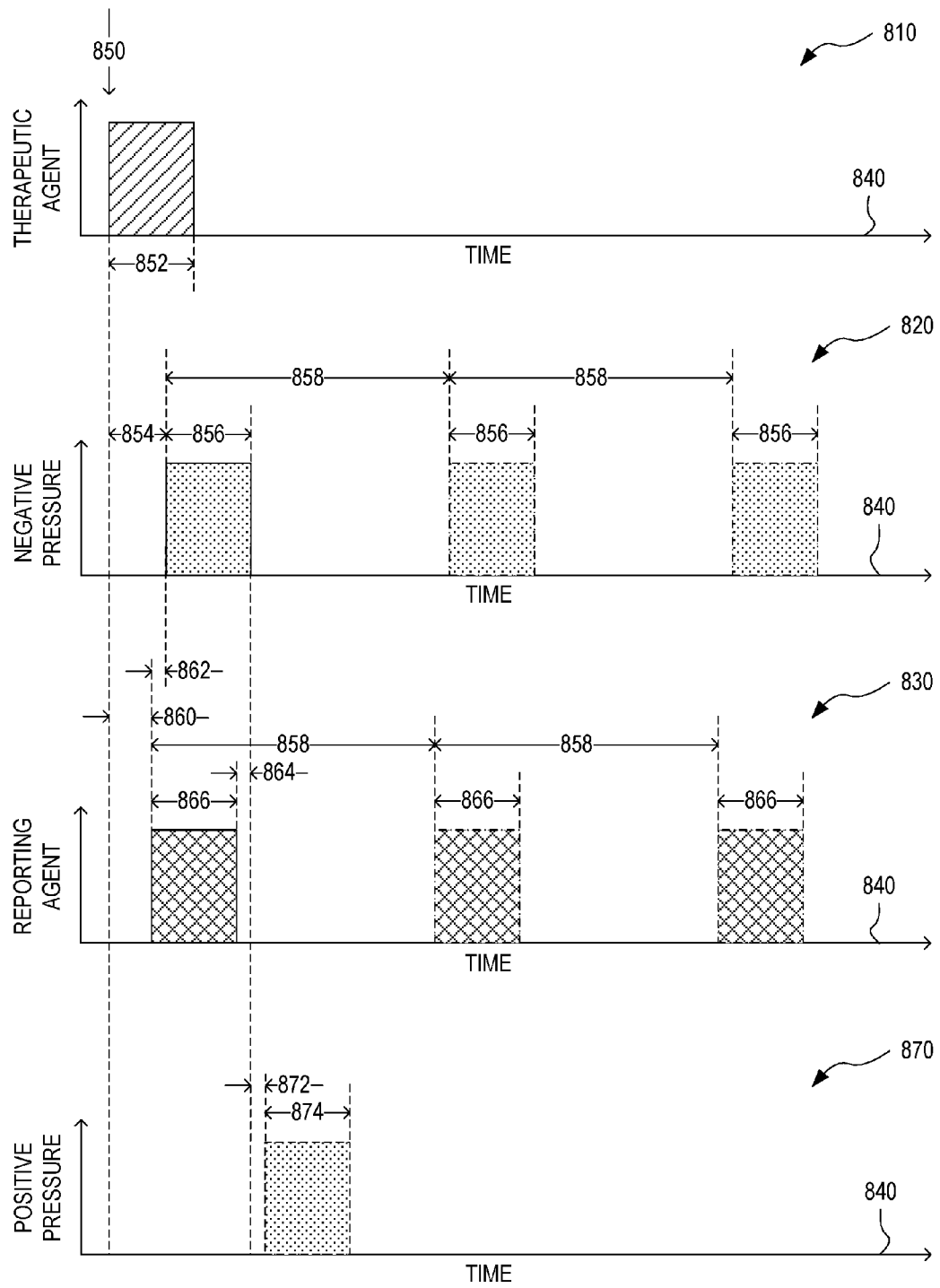
FIG. 8 illustrates exemplary timing of the method of FIG. 7, according to an embodiment.

FIG. 8 illustrates exemplary timing of method 700 (FIG. 7). A diagram 810 shows exemplary administration of a therapeutic agent to the bloodstream as a function of time 840. In one example, diagram 810 shows administration of therapeutic agent 110 (FIG. 1) using delivery device 115. A diagram 820 shows related exemplary application of negative pressure to the disease site as a function of time 840. In one example, diagram 820 shows application of negative pressure 220 (FIG. 2) to disease site 120 by partial enclosure 140 with partial vacuum 145.

At a time 850, method 700 starts step 720 (see diagram 810). Method 700 performs step 720 for a duration 852. Duration 852 is, for example, on the order of seconds, or a fraction of a second. A delay 854 after time 850, step 740 applies negative pressure to the disease site (see diagram 820). Delay 854 may be on the order of seconds. For example, for a 30 centimeter propagation distance to the disease site from the bloodstream location, to which the therapeutic agent is administered, and an average flow rate of 10 centimeters/second, delay 854 is 3 seconds. Step 740 continues for a duration 856 after delay 854. Duration 856 may be identical to or similar to duration 852 to apply the negative pressure for the entire time that the therapeutic agent passes through the area of the disease site. In embodiments of method 700 tailored to enhance uptake of a second pass of recirculated therapeutic agent, step 740 may be repeated at a delay 858 after the first application. Delay 858 is similar to the time between two successive passes of blood through the area of the disease site. Optionally, method 700 may include several such repeats temporally spaced by delay 858.

A diagram 830 shows, as a function of time 840, exemplary detection of a reporting agent administered together with the therapeutic agent. Diagram 830 is related to diagrams 810 and 820. In one example, diagram 830 shows detection of magnetic substance 650 by magnetometer 630, wherein magnetometer 630 is positioned slightly upstream from disease site 120. Detection of the reporting agent occurs at a delay 860 after time 850 and continues for a duration 866 thereafter. Typically, duration 866 is similar to duration 852. In an embodiment of method 700 implementing step 734, step 740 is initiated approximately at delay 860 after time 850 to apply the negative pressure a further delay 862 after delay 860. Diagram 830 illustrates that detection of the reporting agent may be used to determine when to terminate step 740. Step 740 may terminate at a delay 864 after end of duration 866. Delay 864 may be similar to delay 862. In embodiments of method 700 tailored to enhance uptake of a subsequent passes of recirculated therapeutic agent, associated subsequent passes of the reporting agent may be detected after an additional delay 858 after each preceding pass.

A diagram 870 shows optional application of a positive pressure in optional step 750. Method 700 may initiate step 750 after step 740 with a delay 872 between the termination of step 740 and the start of step 750. Delay 872 may be zero, a fraction of a second, in the range from one to a few seconds, or in the range up to many minutes. Method 700 may perform step 750 for a duration 874. Duration 874 may be on order seconds, fractions of a second, about a minute, several minutes, or many minutes.

Although not shown in diagrams 820 and 830, second and subsequent passes of the therapeutic agent may be temporally broadened. Such broadening is due to different sub-volumes of the patient's blood traveling to different areas of the patient and thus experiencing different recirculation times.

Referring now to FIGS. 7 and 8 in combination, method 700 with timing as shown in FIG. 8 may be extended to administration of the therapeutic agent into a vein of the patient, without departing from the scope hereof. If using a vein, the therapeutic agent is diluted into the entire blood volume of the patient also in the first pass.

Figure 9:
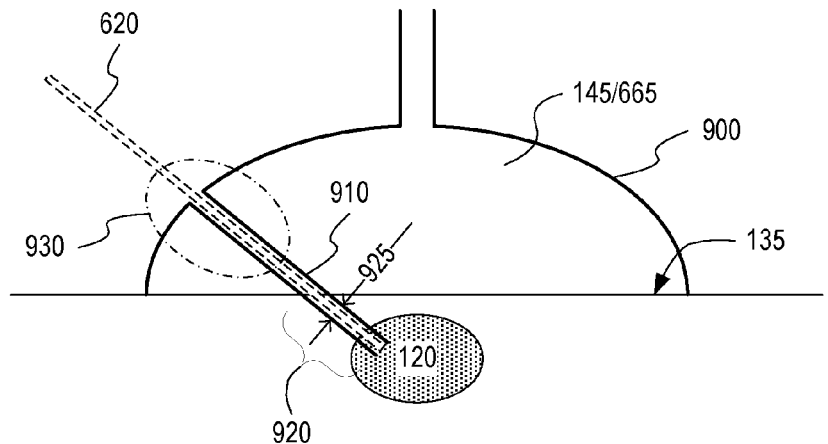
FIG. 9 schematically illustrates a partial enclosure with an integrated port for insertion of one or more sensors into the disease site, according to an embodiment.

FIG. 9 schematically illustrates one exemplary partial enclosure 900 with an integrated port 910 for insertion of one or more sensors 620 (FIG. 6) into disease site 120 (FIG. 1). Partial enclosure 900 is an embodiment of partial enclosure 140, which enables integration of sensor(s) 620 into the partial enclosure, while being capable of maintaining partial vacuum 145 (and/or positive pressure 665) when sealed against patient 130.

Integrated port 910 is configured to penetrate surface 135 and extend into the tissue of patient 130 to disease site 120 or a location near disease site 120. Hence, in operation, a portion 920 of integrated port 910 penetrates surface 135. At least portion 920, and in certain embodiments more or all of integrated port 910, is needle-shaped. Portion 920 may be a straight or tapered needle. Portion 920 has an average outer diameter 925. Average outer diameter 925 may be in the range from 0.1 to 5 millimeters. In one example, average outer diameter 925 is in the range from 0.3 to 2.5 millimeters. In another example, average outer diameter 925 is in the range from 0.3 to 1 millimeter.

In certain embodiments, one or more sensors 620 are integrated into integrated port 910. In one such embodiment, a pressure sensor (such as a Mikro-Tip® Pressure Catheter by Millar, Inc.) is integrated into partial enclosure 900 to form at least portion 920 of integrated port 910. In another such embodiment, a blood perfusion sensor (such as blood flow probe MNP100NX, MNP100NX-3/10, MNP110NX, MNP150NX, or NX-BF/F, all by Oxford Optronix) is integrated into partial enclosure 900 to form at least portion 920 of integrated port 910. In an alternate embodiment, integrated port 910 and portion 920 are configured to accept one or more sensor(s) 620.

In one implementation, partial enclosure 900 includes a flexible portion 930 that allows a range of orientations of integrated port 910. The implementation at least partly decouples the positioning of portion 920 from the overall positioning of partial enclosure 900 on surface 135, to accommodate a variety of possible locations of disease site 120 relative to surface 135 and partial enclosure 900.

Although not shown in FIG. 9, partial enclosure 900 may include several integrated ports 910, without departing from the scope hereof. Furthermore, one or more integrated ports 910 may be used to place magnetometer 650, a susceptometer, and/or an optical fluorescence detector (as discussed in reference to FIG. 6) in disease site 120 or near disease site 120, without departing from the scope hereof. For example, a fiber-based optical fluorescence detector having diameter of 0.5 or up to 1.0 millimeters may be inserted into patient 130 via integrated port 910.

Figure 10:
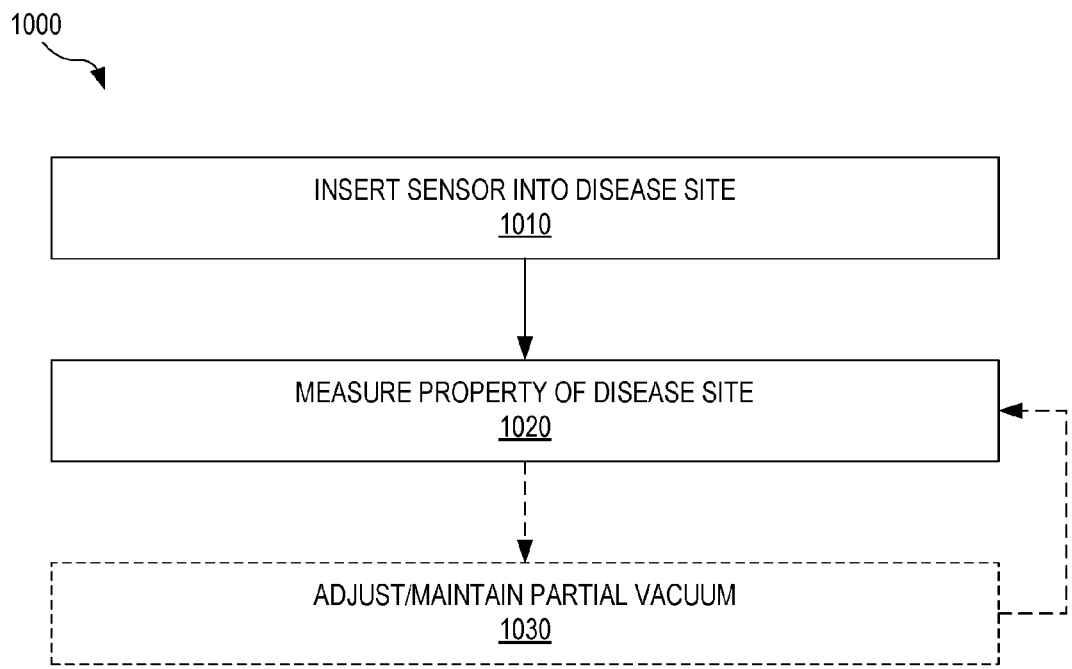
FIG. 10 illustrates a method for manipulating and evaluating at least one property of a disease site to guide the application of negative pressure used to enhance uptake of a therapeutic agent from the bloodstream into the disease site, according to an embodiment.

FIG. 10 illustrates one exemplary method 1000 for manipulating and evaluating at least one property of a disease site to guide the application of negative pressure used to enhance uptake of a therapeutic agent from the bloodstream into the disease site. Method 1000 may be implemented into step 516 of method 500 (FIG. 5) and may be performed by system 600 (FIG. 6).

In a step 1010, method 1000 inserts at least one sensor into the disease site. Each sensor is configured to measure a property of the disease site, such as blood perfusion and/or tissue pressure. In one example of step 1010, one or more sensors 620 are inserted into integrated port 910 of partial enclosure 900 (FIG. 9) and directed to disease site 120. In another example of step 1010, one or more sensors 620 are integrated into partial enclosure 900, as discussed in reference to FIG. 9, and inserted into disease site 120 when partial enclosure 900 is placed on surface 135.

In a step 1020, method 1000 uses the at least one sensor inserted into the disease site in step 1010 to measure at least one property of the disease site, such as tissue pressure and/or blood perfusion. In one example of step 1020, one or more sensors 620 integrated into partial enclosure 900, or inserted through integrated port 910 of partial enclosure 900, measures at least one property of disease site 120. Properties measured by sensor(s) 620 may include tissue pressure and/or blood perfusion.

In a step 1030, method 1000 adjusts or maintains the partial vacuum within the partial enclosure based upon measurements made in step 1020. Thus, step 1030 adjusts or maintains the negative pressure applied by the partial vacuum in the partial enclosure. In one example of step 1030, sensor processing unit 614 evaluates one or more measurements by sensor(s) 620. Based upon such measurements, sensor processing unit 614 may prompt pump control unit 618 to adjust operation of vacuum pump 150 to increase or decrease the strength of partial vacuum 145. If sensor(s) 620 measures a tissue pressure higher (or lower) than a pre-specified value, sensor processing unit 614 may send a signal to pump control unit 618 that leads pump control unit 618 to increase (or decrease) the pumping rate of vacuum pump 150. If sensor(s) 620 measures a blood perfusion rate lower (or higher) than a pre-specified value, sensor processing unit 614 may send a signal to pump control unit 618 prompting pump control unit 618 to increase (or decrease) the pumping rate of vacuum pump 150.

Optionally, method 1000 performs steps 1020 and 1030 in an active feedback loop.

Without departing from the scope hereof, method 1000 may be modified to adjust/maintain a positive pressure in the disease site applied by a positive pressure within the partial enclosure in step 1030. This modified embodiment of method 1000 may be implemented in step 750 of method 700.

Figure 11:
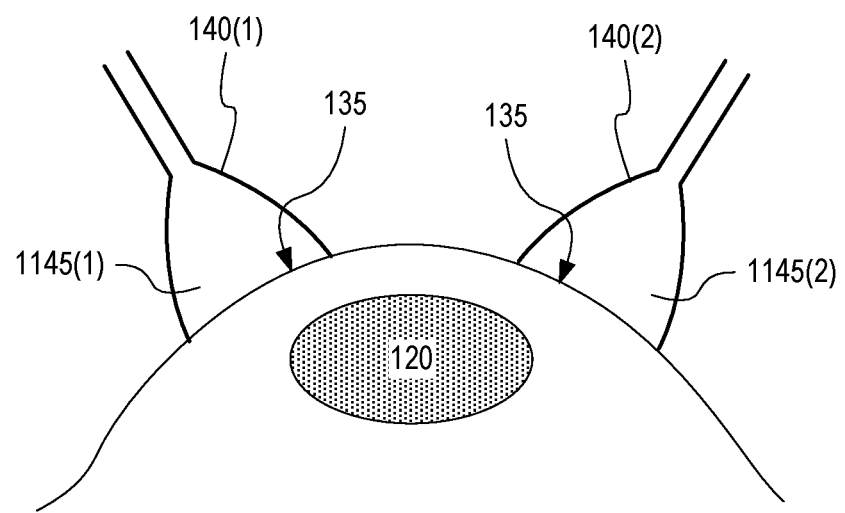
FIG. 11 illustrates two partial enclosures cooperatively configured to apply a pressure gradient to a disease site, according to an embodiment.

FIG. 11 illustrates two exemplary partial enclosures 140 cooperatively configured to apply a pressure gradient to disease site 120. Each partial enclosure is capable of maintaining a pressure 1145 within the partial enclosure, which is different from atmospheric pressure. In a first exemplary scenario, pressure 1145(1) within partial enclosure 140(1) is a negative pressure, and pressure 1145(2) within partial enclosure 140(2) is a positive pressure. In this scenario, disease site 120 experiences a pressure gradient with increasing pressure in the direction from partial enclosure 140(1) to partial enclosure 140(2). In a second exemplary scenario, pressure 1145(1) within partial enclosure 140(1) is a positive pressure, and pressure 1145(2) within partial enclosure 140(2) is a negative pressure. In this scenario, disease site 120 experiences a pressure gradient with increasing pressure in the direction from partial enclosure 140(2) to partial enclosure 140(1). In yet another exemplary scenario, pressures 1145(1) and 1145(2) switch one or more times between the first exemplary scenario and the second exemplary scenario to move around, within disease site 120, a therapeutic agent taken up by disease site 120, so as to improve the distribution of the therapeutic agent throughout disease site 120.

Figure 12:
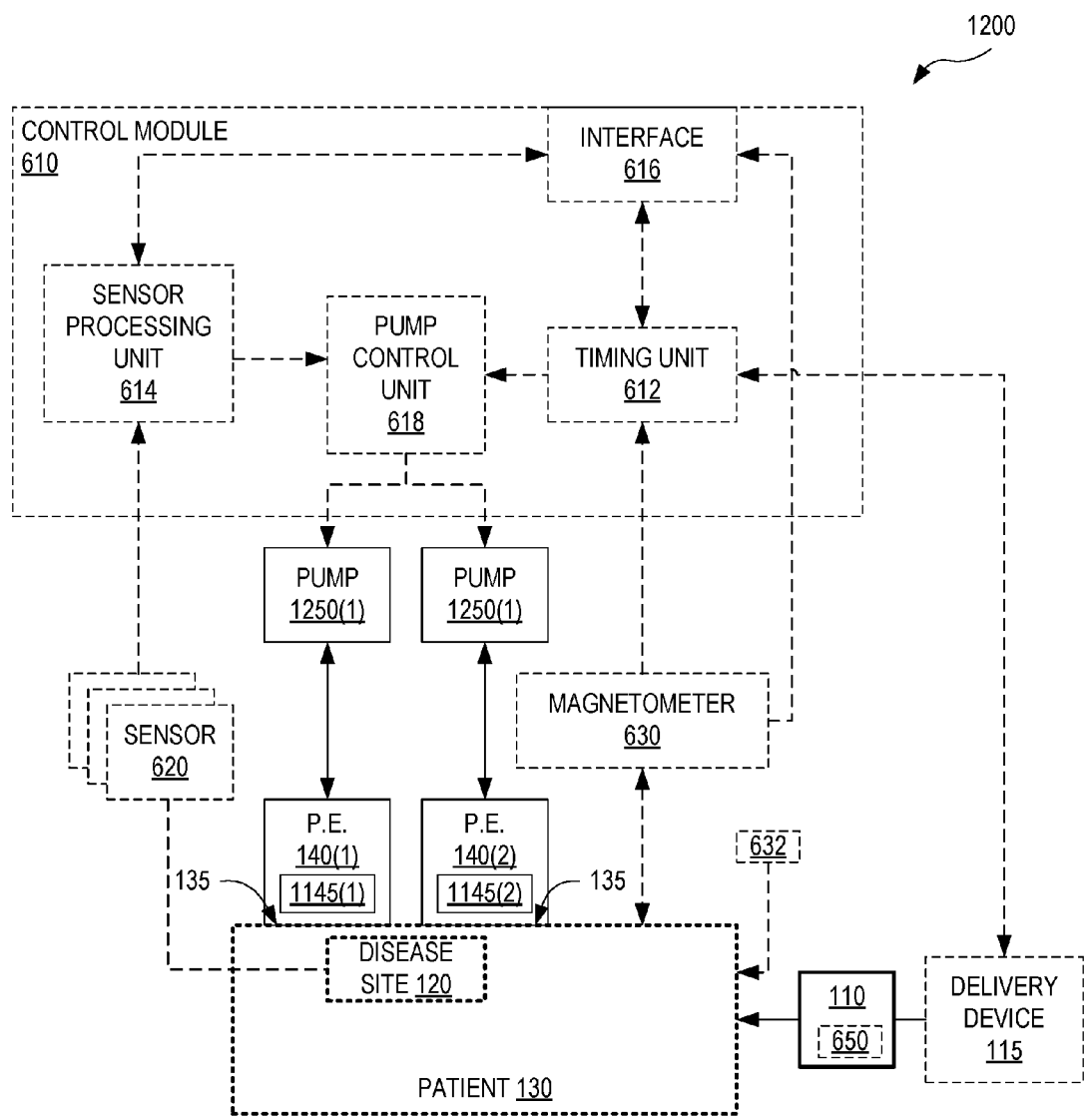
FIG. 12 illustrates a system for enhancing uptake of a therapeutic agent from the bloodstream into a disease site and improving distribution of the therapeutic agent throughout the disease site, according to an embodiment.

FIG. 12 illustrates one exemplary system 1200 for enhancing uptake of a therapeutic agent from the bloodstream into a disease site, such as disease site 120, and improving distribution of the therapeutic agent throughout the disease site. System 1200 is an embodiment of system 100 (FIG. 1) and is similar to system 600 (FIG. 6).

As compared to system 600, partial enclosure 140 and vacuum pump 150 are replaced by two partial enclosures 140 and two pumps 1250. Each pump 1250 is coupled to a respective partial enclosure 140 to maintain pressure 1145 therein. As a result, system 1200 is capable of applying a pressure gradient to disease site 120, as discussed above in reference to FIG. 11. Each of pumps 1250 may be controlled by pump control unit 618, for example according to information received from timing unit 612 and/or sensor processing unit 614.

System 1200 is also capable of applying a negative pressure to disease site 120, for example by activating only one pump 1250 to produce a negative pressure 1145 within one partial enclosure 140, or by activating both pumps 1250 to produce a negative pressure 1145 in both partial enclosures 140. In addition, system 1200 is capable of applying a positive pressure to disease site 120, for example by activating only one pump 1250 to produce a positive pressure 1145 within one partial enclosure 140, or by activating both pumps 1250 to produce a positive pressure 1145 in both partial enclosure 140. System 1200 is thus capable of performing method each of method 500 and 700.

In one embodiment, each pump 1250 is capable of producing both a positive pressure and a negative pressure in a partial enclosure 140 coupled thereto. In another embodiment, system 1200 may be configured with an air handling system that allows for connection of each pump 1250 to either one of partial enclosure 140. In this case, one pump 1250 may be configured for application of negative pressure while the other pump 1250 is configured for application of positive pressure. The pressure gradient across disease site 120 may be reversed by switching which pump 1250 is coupled with which partial enclosure 140.

Figure 13:
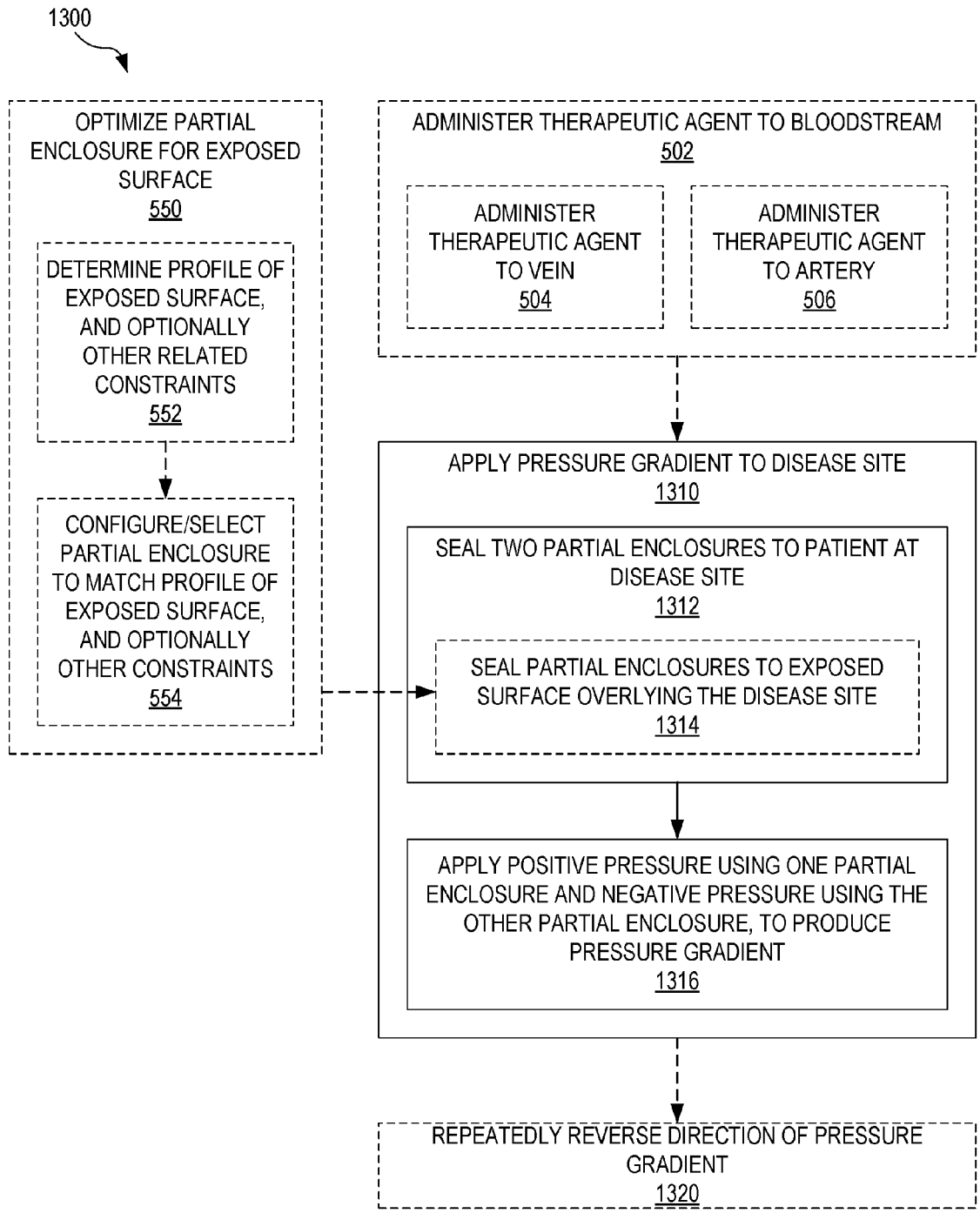
FIG. 13 illustrates a method for applying a pressure gradient to a disease site to improve distribution of a therapeutic agent throughout the disease site, according to an embodiment.

FIG. 13 illustrates one exemplary method 1300 for applying a pressure gradient to a disease site, such as disease site 120, to improve distribution of a therapeutic agent throughout the disease site. Method 1300 is similar to method 500, except that step 510 is replaced by a step 1310. Method 1300 may be performed by system 1200, for example with partial enclosures 140 configured as shown in FIG. 11.

Step 1310 applies a pressure gradient to the disease site. In one example of step 1310, system 1200 applies a pressure gradient to disease site 120. Step 1310 includes steps 1312 and 1316. Step 1312 seals two partial enclosures to the patient at or near the disease site. Optionally, step 1312 includes a step 1314 of sealing the partial enclosures to an exposed surface overlying the disease site, as discussed above for step 514 in reference to FIG. 5. In one example of step 1312, both partial enclosures 140 of system 1200 are sealed to surface 135 of patient 130 at or near disease site 120. Step 1316 applies (a) positive pressure to the tissue of the patient using one partial enclosure and (b) negative pressure to the tissue of the patient using the other partial enclosure. In one example of step 1316, pump 1250(1) is activated to produce a positive pressure 1145(1) in partial enclosure 140(1), and pump 1250(2) is activated to produce a negative pressure 1145(2) in partial enclosure 140(2), Optionally, method 1300 includes a step 1320 of repeatedly reversing the direction of the pressure gradient produced in step 1310. In one example of step 1320, the operation of pump 1250(1) is repeatedly changed to produce a negative pressure 1145(1) in partial enclosure 140(1) in synchrony with the operation of pump 1250(2) being repeatedly changed to produce a positive pressure 1145(2) in partial enclosure 140(2). In another example of step 1320, pump 1250(1) is repeatedly uncoupled from partial enclosure 140(1) and instead coupled with partial enclosure 140(2) and, in synchrony therewith, pump 1250(2) is repeatedly uncoupled from partial enclosure 140(2) and instead coupled with partial enclosure 140(1), without changing the mode of operation of pumps 1250 apart from a possible interruption.

Figure 14:
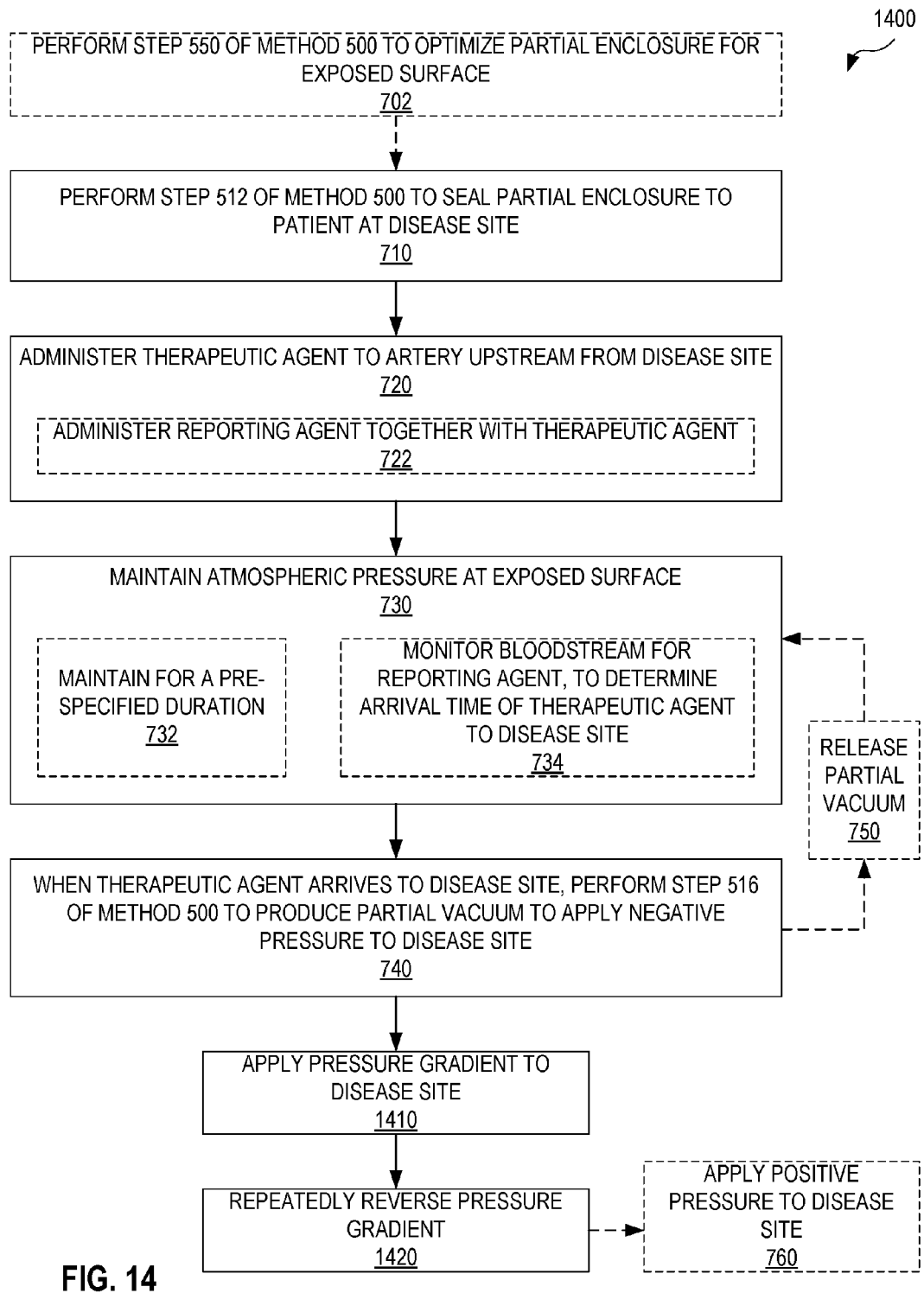
FIG. 14 illustrates a method for enhancing uptake of a therapeutic agent from the bloodstream into a disease site and improving the distribution of the therapeutic agent throughout the disease site, wherein the therapeutic agent is administered to an artery that is upstream from the disease site, according to an embodiment.

FIG. 14 illustrates one exemplary method 1400 for enhancing uptake of a therapeutic agent from the bloodstream into a disease site and improving the distribution of the therapeutic agent throughout the disease site, wherein the therapeutic agent is administered to an artery that is upstream from the disease site. Method 1400 is similar to method 700 except for further including steps 1410 and 1420 between step 740 and optional step 760. Method 1400 may be performed by system 1200, for example with partial enclosures 140 configured as shown in FIG. 11.

Step 1410 performs step 1310 of method 1300 to apply a pressure gradient to the disease site. Step 1420 performs step 1320 of method 1300 to repeatedly reverse the direction of the pressure gradient. Since steps 1410 and 1420 are performed after step 740, the improved distribution of the therapeutic agent is applied to an amount of therapeutic agent enhanced by the performance of step 740. Optionally, method 1400 further performs step 760 after step 1320 to retain a greater amount of the therapeutic agent within the disease site.

Combinations of Features

Features described above as well as those claimed below may be combined in various ways without departing from the scope hereof. For example, it will be appreciated that aspects of one system or method for enhancing uptake of a therapeutic agent from the bloodstream into a disease site, described herein, may incorporate or swap features of another system or method for enhancing uptake of a therapeutic agent from the bloodstream into a disease site, described herein. The following examples illustrate possible, non-limiting combinations of embodiments described above. It should be clear that many other changes and modifications may be made to the systems and methods described herein without departing from the spirit and scope of this invention:

(A1) A method for enhancing uptake of a therapeutic agent from the bloodstream of patient into disease site of the patient may include applying negative pressure to the disease site to form pressure differential favorable for transport of the therapeutic agent from the bloodstream into the disease site.

(A2) In the method denoted as (A1), the disease site may have positive pressure greater than pressure of other adjacent tissue, prior to applying the negative pressure to the disease site.

(A3) In either or both of the methods denoted as (A1) and (A2), the step of applying negative pressure may include reducing the pressure of the disease site such that the pressure of the disease site is less than the pressure of other adjacent tissue.

(A4) In any of the methods denotes as (A1) through (A3), the step of applying may include sealing a partial enclosure to the patient at the disease site, and evacuating air from the partial enclosure to produce a partial vacuum in the partial enclosure.

(A5) In the method denoted as (A4), the step of sealing may include sealing the partial enclosure to an exposed surface of the patient, wherein the exposed surface overlies the disease site.

(A6) In the method denoted as (A5), the disease site may be a non-zero distance away from the exposed surface.

(A7) In the method denoted as (A6), in the step of sealing, the exposed surface may be skin of the patient.

(A8) In the method denoted as (A6), in the step of sealing, the exposed surface may be an internal, surgically-exposed surface of the patient.

(A9) In the method denoted as (A6), in the step of sealing, the exposed surface being an internal surface of the patient accessible through an orifice of the patient.

(A10) The method denoted as (A6) may further include determining the profile of the exposed surface, and configuring the partial enclosure to match the profile.

(A11) In any of the methods denoted as (A4) through (A10), the partial vacuum may be characterized by a negative pressure of magnitude at least as great as magnitude of positive pressure within disease site.

(A12) In any of the methods denoted as (A4) through (A11), the partial vacuum may be characterized by a negative pressure at least as negative as −38 mmHg.

(A13) In any of the methods denoted as (A4) through (A12), the partial vacuum may have magnitude greater than magnitude of positive pressure within disease site, to account for distance between partial enclosure and the disease site.

(A14) Any of the methods denoted as (A1) through (A13) may further include administering the therapeutic agent to the bloodstream.

(A15) In the method denoted as (A14), the step of administering may include administering the therapeutic agent to a vein.

(A16) In the method denoted as (A14), the step of administering may include administering the therapeutic agent to artery upstream of the disease site.

(A17) In the method denoted as (A16), the step of administering may include accessing the artery using a catheter.

(A18) In any of the methods denoted as (A14) through (A17), the step of administering may include starting delivery of the therapeutic agent to the bloodstream at a first time, and the step of applying may include starting application of the negative pressure at a second time that is after the first time and offset from the first time by a first delay.

(A19) In the method denoted as (A18), in the step of applying, the first delay may match propagation time of the therapeutic agent from (a) location of delivery of the therapeutic agent to the bloodstream to (b) the disease site.

(A20) Either or both of the methods denoted as (A18) and (A19) may further include monitoring the bloodstream to determine time of arrival of the therapeutic agent to the disease site, and in the step of applying, the second time may be the time of arrival of the therapeutic agent to the disease site.

(A21) In the method denoted as (A20), the step of administering may include administering, together with the therapeutic agent, a reporting agent to the blood stream, and the step of monitoring may include detecting the reporting agent.

(A22) In the method denoted as (A21), the reporting agent may be a magnetic substance, and the step of monitoring may include measuring at least one of (a) magnetic field and (b) change in response to applied magnetic field.

(A23) In the method denoted as (A22), the step of detecting the magnetic substance may include monitoring, at bloodstream location upstream of the disease site, at least one of (i) magnetic field and (ii) response to applied magnetic field.

(A24) In either or both of the methods denoted as (A22) and (A23), the step of detecting the magnetic substance may include monitoring, at the disease site, at least one of (a) magnetic field and (b) response to applied magnetic field.

(A25) In the method denoted as (A21), the reporting agent may be a fluorescent substance, and the step of monitoring may include monitoring fluorescence.

(A26) Any of the methods denoted as (A1) through (A26) may further include measuring tissue pressure within the disease site using a sensor inserted into the disease site.

(A27) In the method denoted as (A26), the step of applying may include adjusting the negative pressure according to the tissue pressure measured by the sensor.

(A28) Any of the methods denoted as (A1) through (A27) may further include measuring blood perfusion within the disease site using sensor inserted into the disease site.

(A29) In the method denoted as (A28), the step of applying may include adjusting the negative pressure according to the blood perfusion measured by the sensor.

(A30) Any of the methods denoted as (A1) through (A29) may further include, after the step of applying negative pressure, applying positive pressure to the disease site to induce collapse of capillaries of the disease site, so as to improve retention of the therapeutic agent within the disease site.

(A31) Any of the methods denoted as (A1) through (A29) may further include, after the step of applying negative pressure, applying a pressure gradient across the disease site, and repeatedly reversing the pressure gradient to improve distribution of the therapeutic agent throughout the disease site.

(A32) The method denoted as (A31) may further include, after the step of repeatedly reversing, applying positive pressure to the disease site to induce collapse of capillaries of the disease site, so as to improve retention of the therapeutic agent within the disease site.

(B1) A system for enhancing uptake of therapeutic agent from bloodstream of patient into disease site of the patient may include (a) a first partial enclosure with edge configured to interface with an exposed surface, of the patient and overlying the disease site, to seal the first partial enclosure to the exposed surface.

(B2) In the system denoted as (B1), the first partial enclosure may have size sufficient to apply the negative pressure to all of the disease site.

(B3) Either or both of the systems denoted as (B1) and (B2) may further include a first pump configured to evacuate air from the first partial enclosure to produce a partial vacuum in the first partial enclosure, to apply a negative pressure to the disease site so as to enhance uptake of the therapeutic agent into the disease site.

(B4) The system denoted as (B3) may further include a second pump configured to produce a positive pressure within the partial enclosure to apply a positive pressure to the disease site to improve retention of the therapeutic agent by the disease site through capillary collapse.

(B5) The system denoted as (B3) may further include (i) a second partial enclosure with edge configured to interface with the exposed surface to seal the second partial enclosure to the exposed surface and (ii) a second pump for producing a positive pressure within the second partial enclosure to apply, in cooperation with the negative pressure of the first partial enclosure, a pressure gradient to the disease site.

(B6) The system denoted as (B5) may further include and a pump control unit for controlling the operation of the first pump and the second pump to repeatedly reverse direction of the pressure gradient, to improve distribution of the therapeutic agent throughout the disease site.

(B7) Any of the systems denoted as (B1) through (B6) may further include a control module for controlling delay between (a) delivery of the therapeutic agent to the bloodstream and (b) production of a partial vacuum in the first partial enclosure.

(B8) Any of the systems denoted as (B1) through (B7) may further include (i) a magnetometer for detecting magnetic substance propagating through bloodstream together with the therapeutic agent, to determine time of arrival of the therapeutic agent to the disease site, and (ii) a control module for synchronizing first production of the partial vacuum with the arrival.

(B9) Any of the systems denoted as (B1) through (B8) may further include a sensor for measuring property within the disease site, and a needle for inserting the sensor into the disease site.

(B10) In the system denoted as (B9), the needle may be integrated in the first partial enclosure for insertion into the patient inside the first partial enclosure.

(B11) In either or both of the systems denoted as (B9) and (B10), the sensor may be a pressure sensor for measuring pressure within the disease site.

(B12) In either or both of the systems denoted as (B9) and (B10), the sensor may be a blood perfusion sensor for measuring blood perfusion within the disease site.

(B13) Any of the systems denoted as (B1) through (B12) may further include a device for detecting reporting agent propagating through bloodstream together with the therapeutic agent, to determine time of arrival of the therapeutic agent to the disease site.

(B14) The system denoted as (B13) may further includes a control module for synchronizing first production of the partial vacuum with the arrival.

(B15) In either or both of the systems denoted as (B13) and (B14), the device may be configured to detect change in at least one magnetic property, and the reporting agent may include a magnetic substance.

(B16) In either or both of the systems denoted as (B13) and (B14), the device may be an optical fluorescence detector, and the reporting agent may include a fluorescent substance.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present system and method, which, as a matter of language, might be said to fall therebetween.

What is claimed is:

1. A method for enhancing uptake of therapeutic agent from bloodstream of patient into disease site of the patient, comprising:
    sealing a partial enclosure to the patient at the disease site;
    evacuating air from the partial enclosure to produce a partial vacuum in the partial enclosure, thereby applying negative pressure to the disease site to form pressure differential favorable for transport of the therapeutic agent from the bloodstream into the disease site; and
    after the step of evacuating, applying positive pressure to the disease site to induce collapse of capillaries of the disease site, so as to improve retention of the therapeutic agent within the disease site.

2. The method of claim 1, prior to the step of evacuating, the disease site having positive pressure greater than pressure of other adjacent tissue, said applying comprising reducing the pressure of the disease site such that the pressure of the disease site is less than the pressure of other adjacent tissue.

3. The method of claim 1, the step of sealing comprising sealing the partial enclosure to an exposed surface of the patient, the exposed surface overlying the disease site.

4. The method of claim 3, further comprising:
    determining profile of the exposed surface; and
    configuring the partial enclosure to match the profile.

5. The method of claim 3, the disease site being a non-zero distance away from the exposed surface.

6. The method of claim 1, the partial vacuum being characterized by a negative pressure of magnitude at least as great as magnitude of positive pressure within disease site.

7. The method of claim 1, the partial vacuum being characterized by a negative pressure at least as negative as −38 mmHg.

8. The method of claim 1, the partial vacuum having magnitude greater than magnitude of positive pressure within disease site, to account for distance between partial enclosure and the disease site.

9. The method of claim 1, further comprising:
    administering the therapeutic agent to the bloodstream.

10. The method of claim 9, the step of administering comprising administering the therapeutic agent to a vein.

11. The method of claim 9, the step of administering comprising administering the therapeutic agent to artery upstream of the disease site.

12. The method of claim 9,
    the step of administering comprising starting delivery of the therapeutic agent to the bloodstream at a first time; and
    the step of evacuating comprising starting evacuation of the partial enclosure at a second time that is after the first time and offset from the first time by a first delay.

13. The method of claim 12, in the step of evacuating, the first delay matching propagation time of the therapeutic agent from (a) location of delivery of the therapeutic agent to the bloodstream to (b) the disease site.

14. The method of claim 12,
    further comprising monitoring the bloodstream to determine time of arrival of the therapeutic agent to the disease site; and
    in the step of evacuating, the second time being the time of arrival of the therapeutic agent to the disease site.

15. The method of claim 14,
    the step of administering comprising administering, together with the therapeutic agent, a reporting agent to the blood stream; and
    the step of monitoring comprising detecting the reporting agent.

16. The method of claim 1, further comprising:
    measuring tissue pressure within the disease site using a sensor inserted into the disease site; and
    in the step of evacuating, adjusting the negative pressure according to the tissue pressure measured by the sensor.

17. The method of claim 1, further comprising:
    measuring blood perfusion within the disease site using sensor inserted into the disease site; and
    in the step of evacuating, adjusting the negative pressure according to the blood perfusion measured by the sensor.

18. A method for enhancing uptake of therapeutic agent from bloodstream of patient into disease site of the patient, comprising:
    sealing a partial enclosure to the patient at the disease site;
    evacuating air from the partial enclosure to produce a partial vacuum in the partial enclosure, thereby applying negative pressure to the disease site to form pressure differential favorable for transport of the therapeutic agent from the bloodstream into the disease site; and
    after the step evacuating:
    (a) applying a pressure gradient across the disease site, and
    (b) repeatedly reversing the pressure gradient to improve distribution of the therapeutic agent throughout the disease site.

19. The method of claim 18, further comprising after the step of repeatedly reversing:
   applying positive pressure to the disease site to induce collapse of capillaries of the disease site, so as to improve retention of the therapeutic agent within the disease site.

20. A system for enhancing uptake of therapeutic agent from bloodstream of patient into disease site of the patient, comprising:
   a first partial enclosure with edge configured to interface with an exposed surface, of the patient and overlying the disease site, to seal the first partial enclosure to the exposed surface;
   a first pump configured to evacuate air from the first partial enclosure to produce a partial vacuum in the first partial enclosure, to apply a negative pressure to the disease site so as to enhance uptake of the therapeutic agent into the disease site; and
   a second pump configured to produce a positive pressure within the partial enclosure to apply a positive pressure to the disease site to improve retention of the therapeutic agent by the disease site through capillary collapse.

21. The system of claim 20, the first partial enclosure having size sufficient to apply the negative pressure to all of the disease site.

22. The system of claim 20, further comprising a control module for controlling delay between (a) delivery of the therapeutic agent to the bloodstream and (b) production of a partial vacuum in the first partial enclosure.

23. The system of claim 20, further comprising:
   a magnetometer for detecting magnetic substance propagating through bloodstream together with the therapeutic agent, to determine time of arrival of the therapeutic agent to the disease site; and
   a control module for synchronizing first production of the partial vacuum with the arrival.

24. The system of claim 20, further comprising:
   a sensor for measuring property within the disease site; and a needle for inserting the sensor into the disease site.

25. The system of claim 24, the needle being integrated in the first partial enclosure for insertion into the patient inside the first partial enclosure.

26. The system of claim 24, the sensor being a pressure sensor for measuring pressure within the disease site.

27. The system of claim 24, the sensor being a blood perfusion sensor for measuring blood perfusion within the disease site.

28. The system of claim 20, further comprising:
   a device for detecting reporting agent propagating through bloodstream together with the therapeutic agent, to determine time of arrival of the therapeutic agent to the disease site; and
   a control module for synchronizing first production of the partial vacuum with the arrival.

29. The system of claim 28, the device being configured to detect change in at least one magnetic property, and the reporting agent including a magnetic substance.

30. The system of claim 28, the device being an optical fluorescence detector, and the reporting agent including a fluorescent substance.

31. The system of claim 20, further comprising:
   a second partial enclosure with edge configured to interface with the exposed surface to seal the second partial enclosure to the exposed surface;
   a second pump for producing a positive pressure within the second partial enclosure to apply, in cooperation with the negative pressure of the first partial enclosure, a pressure gradient to the disease site;
   and a pump control unit for controlling the operation of the first pump and the second pump to repeatedly reverse direction of the pressure gradient, to improve distribution of the therapeutic agent throughout the disease site.

* * * * *